(12) United States Patent
Agah et al.

(10) Patent No.: US 12,290,564 B2
(45) Date of Patent: *May 6, 2025

(54) METHODS AND APPARATUSES FOR TREATING TUMORS

(71) Applicant: RenovoRx, Inc., Mountain View, CA (US)

(72) Inventors: Ramtin Agah, Menlo Park, CA (US); Kamran Najmabadi, Palo Alto, CA (US); Shaun Bagai, Mountain View, CA (US); Joseph F. Paraschac, Campbell, CA (US)

(73) Assignee: RenovoRx, Inc., Mountain View, CA (US)

( * ) Notice: Subject to any disclaimer, the term of this patent is extended or adjusted under 35 U.S.C. 154(b) by 1004 days.

This patent is subject to a terminal disclaimer.

(21) Appl. No.: 17/315,220

(22) Filed: May 7, 2021

(65) Prior Publication Data

US 2021/0268107 A1   Sep. 2, 2021

Related U.S. Application Data

(63) Continuation-in-part of application No. 16/685,974, filed on Nov. 15, 2019, now Pat. No. 11,052,224, (Continued)

(51) Int. Cl.
*A61B 90/00* (2016.01)
*A61K 31/166* (2006.01)
(Continued)

(52) U.S. Cl.
CPC .......... *A61K 39/3955* (2013.01); *A61B 90/39* (2016.02); *A61K 31/166* (2013.01);
(Continued)

(58) Field of Classification Search
CPC ...... A61M 25/1011; A61M 2025/1013; A61M 2025/1052; A61M 2/02
See application file for complete search history.

(56) References Cited

U.S. PATENT DOCUMENTS

| 4,445,892 A | 5/1984 | Hussein et al. |
| 4,655,746 A | 4/1987 | Daniels et al. |

(Continued)

FOREIGN PATENT DOCUMENTS

| EP | 0402467 A1 | 12/1990 |
| JP | 2017500144 A | 1/2017 |

(Continued)

OTHER PUBLICATIONS

US 7,316,661 B2, 01/2008, Azizi (withdrawn)
(Continued)

*Primary Examiner* — Samuel G Gilbert
(74) *Attorney, Agent, or Firm* — Shay Glenn LLP

(57) ABSTRACT

Apparatuses and methods for treating tumors. A method of treatment may include reducing the microvasculature of a region between a tumor and a lumen through or adjacent to the tumor (e.g., by administering radiation therapy targeting the tumor), isolating a segment of a lumen proximate to the tumor, and administering a dose of a chemotherapeutic agent to the segment.

21 Claims, 11 Drawing Sheets

Related U.S. Application Data which is a continuation of application No. PCT/US2018/033482, filed on May 18, 2018, which is a continuation-in-part of application No. 15/807,011, filed on Nov. 8, 2017, now Pat. No. 10,695,543.

(60) Provisional application No. 62/507,962, filed on May 18, 2017.

(51) Int. Cl.

| | | |
|---|---|---|
| *A61K 31/167* | (2006.01) | |
| *A61K 31/175* | (2006.01) | |
| *A61K 31/282* | (2006.01) | |
| *A61K 31/337* | (2006.01) | |
| *A61K 31/404* | (2006.01) | |
| *A61K 31/407* | (2006.01) | |
| *A61K 31/436* | (2006.01) | |
| *A61K 31/4745* | (2006.01) | |
| *A61K 31/495* | (2006.01) | |
| *A61K 31/502* | (2006.01) | |
| *A61K 31/513* | (2006.01) | |
| *A61K 31/519* | (2006.01) | |
| *A61K 31/573* | (2006.01) | |
| *A61K 31/704* | (2006.01) | |
| *A61K 31/7068* | (2006.01) | |
| *A61K 33/243* | (2019.01) | |
| *A61K 35/28* | (2015.01) | |
| *A61K 38/15* | (2006.01) | |
| *A61K 39/00* | (2006.01) | |
| *A61K 39/395* | (2006.01) | |
| *A61K 45/06* | (2006.01) | |
| *A61K 51/04* | (2006.01) | |
| *A61M 25/00* | (2006.01) | |
| *A61M 25/10* | (2013.01) | |
| *A61M 31/00* | (2006.01) | |
| *A61N 5/10* | (2006.01) | |

(52) U.S. Cl.
CPC .......... *A61K 31/167* (2013.01); *A61K 31/175* (2013.01); *A61K 31/282* (2013.01); *A61K 31/337* (2013.01); *A61K 31/404* (2013.01); *A61K 31/407* (2013.01); *A61K 31/436* (2013.01); *A61K 31/4745* (2013.01); *A61K 31/495* (2013.01); *A61K 31/502* (2013.01); *A61K 31/513* (2013.01); *A61K 31/519* (2013.01); *A61K 31/573* (2013.01); *A61K 31/704* (2013.01); *A61K 31/7068* (2013.01); *A61K 33/243* (2019.01); *A61K 35/28* (2013.01); *A61K 38/15* (2013.01); *A61K 39/0011* (2013.01); *A61K 45/06* (2013.01); *A61K 51/0482* (2013.01); *A61M 25/007* (2013.01); *A61M 25/1011* (2013.01); *A61M 31/005* (2013.01); *A61N 5/10* (2013.01); *A61B 2090/3933* (2016.02); *A61M 2025/1015* (2013.01); *A61M 2025/1052* (2013.01); *A61M 2205/3331* (2013.01)

(56) References Cited

U.S. PATENT DOCUMENTS

| | | |
|---|---|---|
| 4,696,304 A | 9/1987 | Chin |
| 4,714,460 A | 12/1987 | Calderon |
| 4,830,003 A | 5/1989 | Wolff et al. |
| 4,883,459 A | 11/1989 | Calderon |
| 5,281,200 A | 1/1994 | Corso et al. |
| 5,318,535 A | 6/1994 | Miraki |
| 5,338,301 A | 8/1994 | Diaz |
| 5,397,307 A | 3/1995 | Goodin |
| 5,411,479 A | 5/1995 | Bodden |
| 5,415,636 A | 5/1995 | Forman |
| 5,419,763 A | 5/1995 | Hildebrand |
| 5,462,529 A | 10/1995 | Simpson et al. |
| 5,478,309 A | 12/1995 | Sweezer et al. |
| 5,484,412 A | 1/1996 | Pierpont |
| 5,514,092 A | 5/1996 | Forman et al. |
| 5,575,815 A | 11/1996 | Slepian et al. |
| 5,810,757 A | 9/1998 | Sweezer et al. |
| 5,833,644 A | 11/1998 | Azizi et al. |
| 5,833,650 A | 11/1998 | Imran |
| 5,833,672 A | 11/1998 | Kawala et al. |
| 5,836,905 A | 11/1998 | Lemelson et al. |
| 5,836,967 A | 11/1998 | Schneider |
| 5,840,066 A | 11/1998 | Matsuda et al. |
| 5,843,050 A | 12/1998 | Jones et al. |
| 5,888,530 A | 3/1999 | Netti et al. |
| 5,916,193 A | 6/1999 | Stevens et al. |
| 5,919,135 A | 7/1999 | Lemelson |
| 5,919,163 A | 7/1999 | Glickman |
| 5,925,016 A | 7/1999 | Chomenky et al. |
| 5,961,536 A | 10/1999 | Mickley et al. |
| 5,968,012 A | 10/1999 | Ren et al. |
| 6,030,362 A | 2/2000 | Boussignac et al. |
| 6,051,014 A | 4/2000 | Jang |
| 6,083,198 A | 7/2000 | Afzal |
| 6,156,053 A | 12/2000 | Gandhi et al. |
| 6,165,152 A | 12/2000 | Becker et al. |
| 6,176,844 B1 | 1/2001 | Lee |
| 6,287,290 B1 | 9/2001 | Perkins et al. |
| 6,299,598 B1 | 10/2001 | Bander |
| 6,346,098 B1 | 2/2002 | Yock et al. |
| 6,351,663 B1 | 2/2002 | Flower et al. |
| 6,375,634 B1 | 4/2002 | Carroll |
| 6,440,097 B1 | 8/2002 | Kupiecki |
| 6,461,327 B1 | 10/2002 | Addis et al. |
| 6,482,172 B1 | 11/2002 | Thramann |
| 6,485,500 B1 | 11/2002 | Kokish et al. |
| 6,488,672 B1 | 12/2002 | Dance et al. |
| 6,508,777 B1 | 1/2003 | Macoviak et al. |
| 6,520,183 B2 | 2/2003 | Amar |
| 6,569,146 B1 | 5/2003 | Werner et al. |
| 6,569,148 B2 | 5/2003 | Bagaoisan et al. |
| 6,575,932 B1 | 6/2003 | O'Brien et al. |
| 6,589,264 B1 | 7/2003 | Barbut et al. |
| 6,592,546 B1 | 7/2003 | Barbut et al. |
| 6,682,499 B2 | 1/2004 | Lenker |
| 6,685,672 B1 | 2/2004 | Forman |
| 6,692,458 B2 | 2/2004 | Forman et al. |
| 6,699,231 B1 | 3/2004 | Sterman et al. |
| 6,702,781 B1 | 3/2004 | Reifart et al. |
| 6,706,013 B1 | 3/2004 | Bhat et al. |
| 6,706,062 B2 | 3/2004 | Vardi et al. |
| 6,723,070 B1 | 4/2004 | Arai et al. |
| 6,743,196 B2 | 6/2004 | Barbut et al. |
| 6,929,633 B2 | 8/2005 | Evans et al. |
| 6,939,320 B2 | 9/2005 | Lennox |
| 6,986,788 B2 | 1/2006 | Paul et al. |
| 7,150,736 B2 | 12/2006 | Barbut et al. |
| 7,179,251 B2 | 2/2007 | Palasis |
| 7,297,475 B2 | 11/2007 | Koiwai et al. |
| 7,452,532 B2 | 11/2008 | Ali |
| 7,503,904 B2 | 3/2009 | Choi |
| 7,537,562 B2 | 5/2009 | Takano |
| 7,645,259 B2 | 1/2010 | Goldman |
| 7,704,220 B2 | 4/2010 | Solar et al. |
| 7,708,715 B2 | 5/2010 | Gellman |
| 7,780,628 B1 | 8/2010 | Keren et al. |
| 7,815,624 B2 | 10/2010 | Larson |
| 7,887,661 B2 | 2/2011 | Chiu et al. |
| 8,043,257 B2 | 10/2011 | Nguyen et al. |
| 8,088,103 B2 | 1/2012 | Teeslink et al. |
| 8,162,879 B2 | 4/2012 | Hattangadi et al. |
| 8,172,792 B2 | 5/2012 | Wang et al. |
| 8,177,829 B2 | 5/2012 | Benson et al. |
| 8,182,446 B2 | 5/2012 | Schaeffer et al. |
| 8,182,463 B2 | 5/2012 | Chiu et al. |
| 8,187,229 B2 | 5/2012 | Weitzner et al. |

(56) References Cited

U.S. PATENT DOCUMENTS

| | | |
|---|---|---|
| 8,251,948 B2 | 8/2012 | Goldman |
| 8,414,473 B2 | 4/2013 | Jenkins et al. |
| 8,702,678 B2 | 4/2014 | Comerota et al. |
| 8,821,476 B2 | 9/2014 | Agah et al. |
| 8,870,849 B2 | 10/2014 | Steinmetz et al. |
| 9,254,210 B2 | 2/2016 | Bourang |
| 9,457,171 B2 | 10/2016 | Agah et al. |
| 9,463,304 B2 | 10/2016 | Agah et al. |
| 10,099,040 B2 | 10/2018 | Agah et al. |
| 10,286,191 B2 | 5/2019 | Wang et al. |
| 10,512,761 B2 | 12/2019 | Agah et al. |
| 10,695,543 B2 | 6/2020 | Agah et al. |
| 11,052,224 B2 | 7/2021 | Agah et al. |
| 2001/0041862 A1 | 11/2001 | Glickman |
| 2002/0016565 A1 | 2/2002 | Zadno-Azizi et al. |
| 2002/0082548 A1 | 6/2002 | Sanchez et al. |
| 2002/0107471 A1 | 8/2002 | Thompson et al. |
| 2002/0115982 A1 | 8/2002 | Barbut et al. |
| 2003/0147862 A1* | 8/2003 | Buschmann ......... A61K 38/193 514/19.3 |
| 2005/0059930 A1 | 3/2005 | Garrison et al. |
| 2005/0059931 A1 | 3/2005 | Garrison et al. |
| 2005/0149112 A1 | 7/2005 | Barbut |
| 2006/0009798 A1 | 1/2006 | Callister et al. |
| 2006/0149218 A1 | 7/2006 | Slater et al. |
| 2006/0149393 A1 | 7/2006 | Calderon |
| 2006/0173440 A1 | 8/2006 | Lamson et al. |
| 2006/0188442 A1 | 8/2006 | Hallahan |
| 2006/0200075 A1 | 9/2006 | Azizi |
| 2006/0253079 A1 | 11/2006 | McDonough et al. |
| 2007/0010782 A1 | 1/2007 | Doty et al. |
| 2007/0055132 A1 | 3/2007 | Camus et al. |
| 2008/0051660 A1 | 2/2008 | Kakadaris et al. |
| 2008/0058759 A1 | 3/2008 | Makower et al. |
| 2008/0269718 A1 | 10/2008 | Wiener et al. |
| 2009/0018526 A1 | 1/2009 | Power et al. |
| 2009/0043194 A1 | 2/2009 | Barbut |
| 2009/0048577 A1 | 2/2009 | Gillies et al. |
| 2009/0088676 A1 | 4/2009 | Murata |
| 2009/0131866 A1 | 5/2009 | Zhang et al. |
| 2009/0143760 A1 | 6/2009 | Van Dam et al. |
| 2009/0198093 A1 | 8/2009 | Meissner et al. |
| 2009/0198216 A1 | 8/2009 | Muni et al. |
| 2009/0209631 A1 | 8/2009 | Zsebo |
| 2009/0264819 A1 | 10/2009 | Diethrich et al. |
| 2009/0275918 A1 | 11/2009 | Crocker |
| 2010/0016836 A1 | 1/2010 | Makower et al. |
| 2010/0106181 A1 | 4/2010 | Gross et al. |
| 2010/0331815 A1 | 12/2010 | Alt |
| 2011/0093000 A1 | 4/2011 | Ogle et al. |
| 2011/0152683 A1 | 6/2011 | Gerrans et al. |
| 2011/0218494 A1 | 9/2011 | Gerrans et al. |
| 2011/0257577 A1 | 10/2011 | Lane et al. |
| 2011/0282195 A1 | 11/2011 | Solar et al. |
| 2012/0259215 A1 | 10/2012 | Gerrans et al. |
| 2014/0214002 A1 | 7/2014 | Lieber et al. |
| 2014/0276135 A1* | 9/2014 | Agah ................. A61M 25/1011 604/528 |
| 2014/0364835 A1 | 12/2014 | Allen et al. |
| 2015/0018762 A1 | 1/2015 | Fierens et al. |
| 2015/0191546 A1 | 7/2015 | Molldrem et al. |
| 2016/0082178 A1 | 3/2016 | Agah et al. |
| 2018/0169067 A1 | 6/2018 | Bascomb et al. |
| 2020/0206481 A1 | 7/2020 | Agah et al. |
| 2021/0338977 A1 | 11/2021 | Agah et al. |
| 2022/0111184 A1 | 4/2022 | Agah et al. |
| 2023/0302262 A1 | 9/2023 | Agah et al. |

FOREIGN PATENT DOCUMENTS

| | | |
|---|---|---|
| WO | WO02/074178 A2 | 9/2002 |
| WO | WO2014/197362 A1 | 12/2014 |
| WO | WO2015/074045 A2 | 5/2015 |
| WO | WO2016/011328 A1 | 1/2016 |

OTHER PUBLICATIONS

Park et al.; Radiation-induced vascular damage in tumors: implications of vascular damage in ablative hypofractionated radiotherapy (SBRT and SRS). Radiation research; 177(3); pp. 311-327; Mar. 1, 2012.

Jain; Delivery of molecular and cellular medicine to solid tumors; Advanced Drug Delivery Reviews; vol. 64; pp. 353-365; Dec. 1, 2012.

America Cancer Society; Cancer facts and figures, American Cancer Society; 72 pages, retrieved from the internet (https://www.cancer.org/research/cancer-facts-statistics/all-cancer-facts-figures/cancer-facts-figures-2016.html); (year of pub. sufficiently earlier than effective US filing date and any foreign priority date) 2016.

Burkhardt et al; Intra-arterial chemotherapy for malignant gliomas: a critical analysis; Interventional Neuroradiology; 17(3); pp. 286-295; Sep. 2011.

Cancer.Net; Colorectal cancer: stages; 12 pages; retrieved from the internet (https://www.cancer.net/cancer-types/colorectal-cancer/stages) on Jan. 14, 2020.

Cancer.Net; Liver cancer: statistics; 2 pages; retrieved from the internet (https://www.cancer.net/cancer-types/liver-cancer/statistics) on Jan. 14, 2020.

Cancer.Net; Uterine cancer: Statistics; 2 pages; retrieved from the internet (https://www.cancer.net/cancer-types/uterine-cancer/statistics) on Jan. 14, 2020.

Chauffert et al.; Phase III trial comparing intensive induction chemoradiotherapy (60 Gy, infusional 5-FU and intermittent cisplatin) followed by maintenance gemcitabine with gemcitabine alone for locally advanced unresectable pancreatic cancer. Definitive results of the 2000-01 FFCD?SFRO study; Annals of Oncology; 19(9); pp. 1592-1599; Sep. 2008.

Kawaguchi et al; Comparison of neoadjuvant intraarterial chemotherapy versus concurrent chemoradiotherapy in patients with stage IIB uterine cervical cancer; World Journal of Oncology; 4(6); pp. 221-229; Dec. 2013.

Lewandowski et al.; Transcatheter intraarterial therapies: rationale and overview; Radiology; 259(3); pp. 641-657; Jun. 2011.

Mahadevan et al.; Sterotactic body radiotherapy and gemcitabine for locally advanced pancreatic cancer; International Journal of Radiation Oncology*Biology*Physics; 78(3); pp. 735-742; Nov. 2010.

Medgadget; Renovocath for targeted fluid delivery into peripheral vasculature cleared in europe; 3 pages; retrieved from the internet (https://www.medgadget.com/2015/10/renovocath-targeted-fluid-delivery-peripheral-vasculature-cleared-europe.html); Oct. 23, 2015.

Moghanaki; Further evidence of effective adjuvant combined radiation and chemotherapy following curative resection of pancreatic cancer; Gastrointestinal Tumor Study Group; Cancer; 59(12); pp. 2006-2010; (year of pub. sufficiently earlier than effective US filing date and any foreign priority date) 1987.

Multhoff et al.; Radiation-induced changes in microcirculation and interstitial fluid pressure affecting delivery of macromolecules and nanotherapeutics to tumors. Frontiers in Oncology, 2012; 2(165); pp. 1-6, Nov. 2012.

National Cancer Institute; About cancer; 3 pages; retrieved from the internet (https://www.cancer.gov/about-cancer) on Jan. 14, 2020.

Neoptolemos et al; Adjuvant chemoradiotherapy and chemotherapy in resectable pancreatic cancer: a randomised controlled trial; The Lancet; 358(9293); pp. 1576-1585; Nov. 2001.

Renovorx: RenovoCath Animation, delivering what matters: Dec. 17, 2014 (Dec. 17, 2014), Retrieved from the internet: 1 page; URL:https//www.youtube.com/watch?v =?v=LFZ7tvCU2a4&feature= youtube on Jan. 13, 2020.

Renovorx; Researchers report survival benefits with use of renovocath TM in patients with locally advanced pancreatic tumors, 2 pages; retrieved from the internet (https://renovorx.com/researchers-report-survival-benefits-use-renovocath-patients-locally-advanced-pancreatic-tumors/); Apr. 19, 2017.

Sante; Lungcancer prognosis; 3 pages; retrieved from the internet (https://translate.google.com/translate?hl=en&sl=fr&u=http://www.lungcancer-prognosis.com/&prev=search) on Jan. 14, 2020.

(56) References Cited

OTHER PUBLICATIONS

Suryadevra et al; Immunotherapy for malignant glioma; Surgical Neurology International; 6(Suppl 1); S68-S77; Feb. 2015.
Vogl et al.; Regional chemotherapy of the lung: transpulmonary chemoembolization in malignant lung tumors; Seminars in Interventional Radiology; 30(2); pp. 176-184; Jun. 2013.
Wasan; The Emerging Synergy between Radioembolization, Systemic Chemotherapy, and Liver Surgery in Metastatic Colorectal Cancer; European Oncological Disease; 1(1); pp. 52-58; (year of pub. sufficiently earlier than effective US filing date and any foreign priority date) 2007.
Renovorx; RenovoCath } RC120 Receives FDA 510(k) Clearance; 3 pages; retrieved from the internet (https://renovorx.com/renovocath-rc120-receives-fda-clearance/); Oct. 30, 2014.
Renovorx; Wayback Machine: RenovoCath } RC120—RenovoRx; 7 pages; retrieved from the internet. (https://web.archive.org/web/20230000000000*/renovorx.com/wp-content/uploads/2016/07/MTK-5001.pdf); Apr. 25, 2017.
Agah et al.; U.S. Appl. No. 18/149,649 entitled "Methods for delivery of therapeutic materials to treat cancer," filed Jan. 3, 2023.

* cited by examiner

METHODS AND APPARATUSES FOR TREATING TUMORS

CROSS REFERENCE TO RELATED APPLICATIONS

This patent application claims priority as continuation-in-part to U.S. patent application Ser. No. 16/685,974, filed on Nov. 15, 2019, titled "METHODS FOR TREATING CANCEROUS TUMORS," which is a continuation of International Patent Application No. PCT/US2018/033482, filed on May 18, 2018, titled "METHODS FOR TREATING CANCEROUS TUMORS," now International Publication No. WO 2018/213760, which claims priority to U.S. Provisional Patent Application No. 62/507,962, filed on May 18, 2017 titled "METHODS FOR TREATING CANCEROUS TUMORS," each of which is herein incorporated by reference in its entirety.

International Patent Application No. PCT/US2018/033482 also claims priority as a continuation-in-part of U.S. patent application Ser. No. 15/807,011, filed on Nov. 8, 2017, titled "METHODS FOR TREATING CANCEROUS TUMORS," now U.S. Pat. No. 10,695,543, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Cancer begins when a cell begins dividing uncontrollably. Eventually, these cells form a visible mass or tumor. Solid tumors are masses of abnormal tissue that originate in organs or soft tissues that typically do not include fluid areas. Examples of solid tumors include: pancreatic cancer, lung cancer, brain cancer, liver cancer, uterine cancer, and colon cancer.

Traditionally, tumors have been treated with surgical resection, radiation, and/or chemotherapy. Surgical resection involves the removal of tumor tissue. Radiation uses beams of intense energy to kill cancer cells and to shrink tumors. And chemotherapy involves the use of therapeutic agents or drugs to treat cancer. But surgical resection may not completely remove a tumor. Radiation and chemotherapy can have undesirable systemic side effects, including extreme fatigue, hair loss, infection, nausea and vomiting, and others that limit their usefulness. More recently, direct activation of the patient's immune system to attack cancerous cells has shown promise in treating certain solid tumors, but not all. Thus, the need for an improvement in both the safety and the efficacy of current therapy still exists.

Use of localized intra-arterial therapies, including trans-arterial chemo-delivery (TAC) or trans-arterial chemo-embolization (TACE), has been shown to be clinically beneficial for a certain subset of solid tumors. TAC or TACE can involve imaging an organ having a tumor using angiography, isolating a branch of the artery that feeds the tumor or portion of the organ containing the tumor, and then locally injecting chemotherapy in a bolus fashion via the isolated artery. Localized intra-arterial therapies allow higher drug concentration to reach the tumor, overcoming the problem of poor blood flow to tumor mass in comparison to healthy tissue. Furthermore, localized intra-arterial therapies can also take advantage of the first pass effect of chemotherapeutics by generating higher level drug concentrations at the tumor cell membrane and therefore enhancing cellular drug uptake as compared to non-localized infusion. Lastly, local delivery can reduce systemic side effects of chemotherapy.

One of the limitations of TAC and TACE is the need for selective cannulation and isolation of the tumor feeder vessel or arterial branch that can target the smallest portion of the organ containing the tumor. But it may be difficult to target and limit drug delivery to a small portion of the organ containing the tumor while achieving desired efficacy levels with the cancer treatment. On the one hand, limiting drug delivery to a small portion of the organ can reduce the potential impact of the administered drug on surrounding healthy tissue. But on the other hand, when the isolated region becomes too small, drug uptake levels by the tumor may decrease and reduce the efficacy of the cancer treatment. Given these limitations, a method to deliver a sufficient dose of a chemotherapeutic drug in addition to and independent of the need to cannulate and isolate to a specific feeding/supplying branch of a tumor feeder vessel is highly desirable.

In 2016, pancreatic cancer ranked as the fourth leading cause of cancer death in the United States, and the tenth most commonly diagnosed tumor type in men and women. Estimates of incidence and deaths caused by pancreatic cancer are approximately 53,070 and 41,780, respectively (American Cancer Society: Cancer Facts and Figures, American Cancer Society, 2016). Projections based on the changing demographics of the United States population and changes in incidence and death rates reveal that, unless earlier diagnosis is made possible or better treatment options become available, pancreatic cancer is anticipated to move from the fourth to the second leading cause of cancer death in the United States by 2020.

Systemic chemotherapy as treatment for pancreatic cancer may be modestly effective due to low drug penetration in the pancreas because a drug infused systemically only moderately penetrates the pancreas, which may generally increase toxicity within a patient's body but not have an effect on the cancer. In many instances, tumors located in the pancreas are located in tissue surrounding an artery but not in a region of an artery that can be targeted and isolated. Accordingly, it may be difficult for a biologic agent or drug to reach and treat the tumors. Among solid tumors, drug delivery to pancreatic tumors is especially difficult due to the hypo-vascular and poorly perfused nature of the pancreas. The unique environment of the pancreas lends itself to reduced drug levels within the organ tissue, which reduces the effectiveness of systemic chemotherapy that relies on a functional vasculature for delivery to tumor cells. Also, the effect of chemotherapy is concentration dependent, and systemic infusion oftentimes results in low concentrations. Aside from dosing limitations in treating pancreatic cancer, many systemic side effects of chemotherapeutic agents can result from the treatment.

In an attempt to increase the effectiveness of chemotherapeutic agents on pancreatic tumors while decreasing systemic toxicity, various researchers have delivered drugs directly to the pancreas using traditional endovascular catheters. These initial attempts have been limited due to the redundant nature of blood supply to the pancreas and its adjacent organs. Non-selective engagement of the pancreatic vessels can also lead to the wash through of chemotherapy to other adjacent organs. Most of the arterial branches to the pancreas are small; thus, selective engagement of these small branches via conventional catheters is difficult. Thus, there is a need to address these and other deficiencies.

Lung cancer is another deadly cancer that is difficult to treat. Lung cancer is responsible for 23% of total cancer deaths. Long-term exposure to tobacco smoke causes 80 to 90% of lung cancers. Nonsmokers account for 10 to 15% of lung cancer cases, and these cases are often attributed to a combination of genetic factors or other environmental exposures (Vogl, T. J., et al., *Seminars in Interventional Radiology*, 2013, 30(2): 176-184).

Common treatments for lung cancer depend on the cancer's specific pathology, staging, and the patient's performance status (e.g., ability to breath). Traditional treatment options are surgery, chemotherapy, immunotherapy, radiation therapy, and palliative care. Intravascular techniques for localized delivery of chemotherapeutic agents have also been used to treat lung cancer, and include cancer therapy such as arterial chemoembolization, bronchial artery infusion (BAI), isolated lung perfusion (ILP), and lung suffusion. Chemotherapeutics approved for the treatment of non-small cell lung cancer in the United States include methotrexate, paclitaxel albumin-stabilized nanoparticle formulation, afatinib dimaleate, everolimus, alectinib, pemetrexed di sodium, atezolizumab, bevacizumab, carboplatin, ceritinib, crizotinib, ramucirumab, docetaxel, erlotinib hydrochloride, gefitinib, afatinib dimaleate, gemcitabine hydrochloride, pembrolizumab, mechlorethamine hydrochloride, methotrexate, vinorelbine tartrate, necitumumab, nivolumab, paclitaxel, ramucirumab, and osimertinib, and the combinations carboplatin-taxol and gemcitabine-cisplatin (https://www.cancer.gov/aboutcancer). Drugs approved for the treatment of small cell lung cancer include methotrexate, everolimus, doxorubicin hydrochloride, etoposide phosphate, topotecan hydrochloride, mechlorethamine hydrochloride, and topotecan (https://www.cancer.gov/aboutcancer). Lung cancer such as small cell lung cancer can sometimes be treated with a combination of radiation therapy and one or more chemotherapeutics. But other types of lung cancer such as non-small cell lung cancer may not be sensitive to current chemotherapeutics. In many instances, current treatment methods are not effective at providing meaningful treatment or palliative care. Thus, it is desirable to have a more effective method for treating lung cancer tumors.

Malignant gliomas comprise up to 80% of primary malignant brain tumors in the adults. Among these, glioblastomas are the most deadly and account for 82% of all malignant gliomas (Suryadevra, C. M., et al., *Surg. Neurol. Int.,* 2015, 6(1): S68-S77). The current standard of care includes surgical resection, followed by adjuvant external beam radiation and chemotherapy with drugs such as temozolomide. Conventional therapy is nonspecific and often results in a tragic destruction of healthy brain tissue. These treatments can be incapacitating and produce a median overall survival of just twelve to fifteen months. In addition, the invasive properties of glioblastomas make complete resection difficult, and the glioblastomas may recur following initial treatment. Malignant gliomas are also highly vascularized tumors, and their unique capacities for regulating angiogenesis contribute to their resistance against known therapies.

Malignant gliomas, including glioblastoma multiforme, have been treated with inter-arterial chemotherapy. Typically, a catheter is inserted in the femoral artery and ends in the carotid artery, while a separate microcatheter is also inserted into the femoral artery and used to explore the specific vessels feeding the tumor for administration of the chemotherapy (Burkhardt, J-K., et al., *Interventional Radiology,* 2011, 17:286-295). But such methods are not always effective and can be improved.

Liver cancer is another difficult-to-treat cancer characterized by solid tumors. In 2016, an estimated 39,230 adults (28,410 men and 10,820 women) in the United States will be diagnosed with primary liver cancer. Liver cancer also commonly metastasizes to other parts of the body. It is estimated that 27,170 deaths (18,280 men and 8,890 women) from this disease will occur this year. Liver cancer is the tenth most common cancer and the fifth most common cause of cancer death among men. It is also the eighth most common cause of cancer death among women (American Cancer Society: Cancer Facts and Figures, American Cancer Society, 2016). When compared with the United States, liver cancer is much more common in developing countries within Africa and East Asia. In some countries, it is the most common cancer type. The one-year survival rate for people with liver cancer is 44%. The five-year survival rate is 17%. For the 43% of people who are diagnosed at an early stage, the five-year survival rate is 31%, while it is only 11% if the cancer has spread to surrounding tissues or organs and/or the regional lymph nodes. If the cancer has spread to a distant part of the body, the 5-year survival rate is only 3% (http://www.cancer.net/cancer-types/lliver-cancer/statistics).

Currently, patients with hepatocellular carcinoma and cirrhosis are frequently treated with non-specific trans-arterial therapy using techniques that deliver treatments directly into the liver (Lewandowski, R. J., et al., *Radiology,* 2011, 259(3): 641-657). Physicians use the femoral artery to gain access to the hepatic artery, one of two blood vessels that feed the liver. Trans-arterial therapy such as TACE involves delivery of chemotherapy directly to the liver, followed by a process to embolize the chemotherapy. In this therapy, a thick, oily substance (for example, Lipiodol) is mixed with chemotherapy (for example, floxuridine, sorafenib tosylate or a mixture of platinol, mitomycin, and adriamycin) and injected under radiological guidance directly into the artery supplying the tumor via a catheter. The Lipiodol, or other particles, helps to contain the chemotherapy within the tumor and blocks further blood flow, thus cutting off the tumor's food and oxygen supply. TACE with doxorubicin-filled beads delivers the beads directly to the liver, which releases chemotherapy slowly over time and also blocks the blood flow to the tumor. In a similar therapy, radioactive yttrium beads are delivered via a catheter into the hepatic artery. The beads deliver radiation to the tumor, which kills the tumor cells, although other unintended areas of the liver may also receive radiation, creating undesirable destruction of healthy tissue. Thus, there is a need to improve current treatment methods.

In 2016, an estimated 60,050 women in the United States were diagnosed with uterine endometrial cancer, with an estimated 10,470 deaths occurring (http://www.cancer.net/cancer-types/uterine-cancer/statistics). Uterine cancer is the fourth most common cancer for women in the United States. The incidence of endometrial cancer is rising, mainly due to a rise in obesity, which is an important risk factor for this disease. It is the sixth most common cause of cancer death among women in the United States with the 5-year survival rate being 82%.

Concurrent chemoradiotherapy (CCRT) is the main treatment for locally advanced cervical cancer. Neoadjuvant chemotherapy (NAC) was widely employed until CCRT became the standard, and conflicting results have been reported. Neoadjuvant intra-arterial chemotherapy (IANAC) is another method for delivering NAC as an alternative to systemic chemotherapy. IANAC has been reported to achieve beneficial results that cannot be obtained by systemic chemotherapy or CCRT. Kawaguchi et al. have reported that IANAC with cisplatin followed by radical hysterectomy or radiotherapy afforded similar results to concurrent chemoradiotherapy for stage IIIB cervical cancer (Kawaguchi et al., *World Journal of Oncology*, 2013, 4(6): 221-229). Drugs approved for use in the United States for the treatment of cervical cancer include bevacizumab, bleomycin, and topotecan hydrochloride, and the combination gemcitabine-cisplatin. Uterine cancer of endometrial origin may be treated with, for example, megestrol acetate. But many systemic side effects of chemotherapeutic agents can result from current treatment methods. It is desirable to have a specific means of targeting uterine tumors.

In the United States, colorectal cancer is the fourth most common cancer diagnosed each year for all adults combined. Separately, it is the third most common cancer in men and third most common cancer in women. In 2016, an estimated 134,490 adults in the United States were diagnosed with colorectal cancer, with 95,270 new cases of colon cancer and 39,220 new cases of rectal cancer. It is estimated that 49,190 deaths (26,020 men and 23,170 women) were attributed to colon or rectal cancer in 2016. Colorectal cancer is the second leading cause of cancer death in the United States, although when it is detected early, it can often be cured. The death rate from this type of cancer has been declining since the mid-1980s, probably because of an improvement in early diagnosis. The 5-year survival rate colorectal cancer is 65%, while the 10-year survival rate is 58% (http://www.cancer.net/node/18707).

When possible, surgical removal of colorectal tumors is the treatment of choice as it can eliminate the cancer completely. However, metastasis to other organs, particularly the liver and the lung, is common and complicates the treatment of colon and rectal cancer dramatically. It is therefore desirable to have a method of treating metastasized colon and rectal cancers that are present in other organs of the body. Drugs approved for use in treating colon cancer in the United States include bevacizumab, irinotecan hydrochloride, capecitabine, cetuximab, ramucirumab, oxaliplatin, 5-FU, fluorouracil, leucovorin calcium, trifluridine, tipiracil hydrochloride, oxaliplatin, panitumumab, ramucirumab, regorafenib, ziv-aflibercept and the combinations capox, folfiri-bevacizumab, folfiri-cetuximab, FU-LV, xeliri and xelox.

SUMMARY OF THE DISCLOSURE

Described herein are apparatuses (e.g., systems, devices, etc.) and methods for the treatment of tumors, including cancerous tumors. These methods may include: administering a course of radiation therapy targeting an area including a solid tumor; waiting a period of time for the radiation to take effect on the vasculature in the area; and administering a therapeutically effective dose of a chemotherapeutic agent to an isolated arterial section near the solid tumor.

For example, these methods may include administering a targeted dose of radiation to an area including a solid tumor, waiting a period of time, and isolating an area containing a cancerous tumor by, for example, isolating an arterial segment proximate to the tumor; and administering a localized therapeutically effective dose of a chemotherapeutic agent.

The method may include administering a course of radiation therapy to an area including a solid tumor; isolating the proximal and the distal part of the vasculature closest to the tumor to produce an isolated arterial segment; decreasing the intraluminal pressure of the isolated arterial segment to the level of the interstitium; and administering a therapeutically effective dose of a chemotherapeutic drug. The method may include an additional step of waiting a period of time following the step of administering the course of radiation therapy.

In some examples the method includes delivering radiation therapy to a target area including a tumor; and inserting a catheter device into an artery where the catheter device includes a first occlusion member, a second occlusion member, and a body defining a lumen in fluid communication with an infusion port. The infusion port is disposed between the first occlusion member and the second occlusion member. The first occlusion member and the second occlusion member are moved to an area of the artery disposed proximate to the target area. The first occlusion member and the second occlusion member are deployed to isolate the area of the artery disposed proximate to the target area. A dose of chemotherapeutic agent may then be delivered to the isolated area of the artery via the lumen and the infusion port. The chemotherapeutic agent permeates to the target area including the tumor from the isolated area of the artery.

In some embodiments, the method includes administering a dose of radiation to a target area including a tumor; inserting a catheter device into a vessel, the catheter device including a first occluder and a second occluder; isolating a segment of the vessel proximate to the target area using the first occluder and the second occluder; and delivering a dose of an agent to the segment via the catheter device.

In some embodiments, the method includes administering a dose of radiation to a target area including a tumor; isolating a segment of the vessel proximate to the target area; adjusting an intraluminal pressure of the segment to a level of pressure of an interstitial space between the vessel and the target area; and delivering a dose of an agent to the segment via the catheter device.

In general, the methods described herein may pre-treat the tissue (including tumor tissue) with radiation to reduce the microvasculature, which may limit or prevent washout of the applied chemotherapeutic(s). Any of these methods may further include blocking or otherwise excluding side branches of the vasculature at or around the target tissue. For example, one or more coils may be used to exclude a side branch. In some examples, a glue or sealant may be used.

The application of radiation may be local to the target tissue. For example, a local radiation catheter may be used.

Alternatively or additionally other micro-vasculature closure or reduction techniques may be used. For example, one or more drug agents may be used. As mentioned, one or more glue and/or sealants may be used. The glue/sealant may be drug absorbent. In some examples, the glue/sealant may be drug eluting. In some examples, energy, such as ultrasound energy, may be used to reduce and/or close the micro-vasculature to the target tissue region.

Following reduction and/or inhibition of the function of the microvasculature in the target tissue (including the tissue of and/or surrounding a tumor), which may include waiting a period of time for the reduction and/or inhibition to occur, the chemotherapeutic agent may be applied to the target tissue by using two or more occluders within a lumen (including but not limited to the vasculature, such as arterial vasculature and venous vasculature) in or adjacent to the target tissue, so that the chemotherapeutic agent may be applied locally, e.g., under controlled pressure, to the target tissue.

Virtually any tumor tissue may be treated as described herein. An apparatus including two or more occluders may be used in any appropriate lumen within or adjacent to the target tumor(s). These apparatuses may generally be referred to as catheter devices. For example, the methods described herein may include using an apparatuses including two or more occluders for delivery of the therapeutic agent (e.g., chemotherapeutic) agent(s) may be used in a target lumen comprising an artery such as, but not limited to: gastroduodenal artery, pulmonary artery, proper hepatic or left or right hepatic artery, superior mesenteric artery, celiac artery, inferior vesical artery, middle rectal artery, internal pudendal artery, pulmonary artery (and its sub-branches), uterine artery, arteries of the bladder (e.g., superior vesical branch of the internal iliac artery, inferior vesical artery, vaginal artery, obturator and inferior gluteal arteries), mesenteric artery, iliac artery (and its sub-branches), and/or the internal carotid artery (and it's sub-branches). The methods described herein may also include using an apparatus including two or more occluders as described herein to deliver a therapeutic agent (e.g., a chemotherapeutic agent) in a target lumen such as, but not limited to: a vein, a bronchial lumen, a lumen of the digestive tract (esophagus, stomach, duodenum, small intestine, colon, rectum, etc.), a lumen of the bile duct (e.g., cholangio and pancreas), a urethra, a fallopian tubes, etc.

Any appropriate chemotherapeutic agent may be used, including, but not limited to small molecule chemotherapeutic agents, immunochemotherapeutic agents, stem cells, hormones, particles (nanoparticles, microparticles, etc.) and combinations of these. For example, the chemotherapeutic agent may include one or more (including combinations) of: Paclitaxel, Abraxane, Everolimus, Erlotinib Hydrochloride, Fluorouracil, Irinotecan Hydrochloride, Olaparib, Mitomycin, Irinotecan Hydrochloride Liposome, Sunitinib Malate, Lanreotide Acetate, and Lutetium Lu 177-Dotatate. Examples of combinations include, but not limited to: Folfirinox (Leucovorin Calcium {Folinic Acic}-Fluorouracil-Irinotecan Hydrochloride-Oxaliplatin), Gemcitabine-Cisplatin, Gemcitabine-Oxaliplatin, and OFF (Oxaliplatin-Fluorouracil-Leucovorin Calcium {Folinic Acic}). Other chemotherapeutic agents may include one or more (including combinations) of: alkylating agents, Nitrosoureas, Antimetabolites, Anti-tumor antibiotics, Topoisomerase Inhibitors, Mitotic Inhibitors, Corticosteroids, All-trans-retinoic acid, Arsenic trioxide, Asparaginase, Eribulin, Hydroxyurea, Ixabepilone, Mitotane, Omacetaxine, Pegaspargase, Procarbazine, Romidepsin, Vorinostat, All-trans-retinoic acid, Cisplatin, Entrectinib, Larotrectinib Sulfate, Nitrosourea, Pembrolizumab, Temozolomide, Carmustine, Bevacizumab, Naxitamab, and Lomustinc.

Other chemotherapeutic agents may include one or more (including combinations) of: tumor antigen, immunotherapy agents, immunomodulators (e.g., thalidomide, lenalidomide, pomalidomide, etc.), stem cells, radiotherapy particles, steroids, hormones, coagulants, sclerosing agents (e.g., doxycycline, thiotepa, bleomycin, minocycline, 5-fluorouracil, etc.), cross-linking agents, etc.

Any of the agents described above may be used in combination with each other and/or in combination with a contrast media for fluoroscopic visualization.

In practice, the methods described herein may include isolating the lumen within or immediately adjacent to the target tissue using any of the apparatuses described herein. These apparatuses may generally include two (or in some examples, more, such as three, four, etc.) occcluders that may occlude the lumen to prevent flow in/out of the lumen and allow the local control of pressure within the lumen by applying material, such as fluid and/or chemotherapeutic agent, into the portion of the lumen blocked off by the two or more occluders. The occluders may be adjustable, including the spacing between the occluders.

In one non-limiting example, the method may include isolating the lumen segment, such as an arterial segment, with a pair of occludes (such as, in one example a pair of balloon occccluders) and adjusting the length between the occluders. The isolated segment (e.g., the isolated arterial segment) may then be filled with fluid including the chemotherapeutic agent at a controlled pressure for a controlled period of time, to deliver the chemotherapeutic agent into the target tissue, while preventing or reducing wash out because the microvasculature has been inhibited as described above.

Alternatively or additionally, in some examples described herein, the apparatus for use with any of these methods may include a fixed distance between the two or more occluders. The apparatus may be chosen from a variety of apparatuses each having a specified length between the two (or more) occluders. The user (e.g., physician) may select the appropriate size based on the anatomy, which may be visualized prior to or during the procedure using CT scan ultrasonography, fluoroscopy, MRI, x-ray, or other imaging means known in the art.

In general, an occluder is an expandable structure (frame, balloon, etc.) that seals off the lumen to prevent flow of fluid past the occluder within the lumen, when the occluder is deployed. The occluder may have a deployed configuration which is expanded to occlude the lumen (and seal it at one site) and a delivery configuration in which the occluder is collapsed to a smaller profile. Examples of occluders include, but are not limited to balloons, umbrellas, expandable frames or meshes that may support a sealing membrane, etc. For example, an occluder may be configured as an expandable parachute structure and/or as an expandable umbrella. In some examples the occluder is an expandable stent having one or more membranes within the stent body that prevent the flow of material (fluid, such as blood, etc.) through the expanded stent (fully or partially covered with an impermeable or semi-permeable coating) once deployed. In some cases, the occluder includes an expandable (e.g., nitinol, stainless steel, etc.) frame that supports a sealing membrane. The sealing membrane may be a polymeric material.

Any of these apparatuses (and methods of using them) may include pressure monitoring. In particular, the pressure between the occluders may be monitored. Pressure monitoring may include in-line monitoring using one or more pressure sensors positioned on the handle of the apparatus, in fluid communication with one or more openings into the region between the occluders that can therefore detect pressure within the isolated region of the lumen. One or more additional pressure sensors may be used to determine the pressure within all or some of the occluders, particularly in occludes that are expanded by fluid pressure. The fluid pressure within the isolated region of the lumen may be estimated (e.g., using a controller of the apparatus), and/or may be displayed, stored, transmitted, including wirelessly transmitted, and/or may be used as feedback to control the pressure within the isolated region of the lumen. For example, the pressure of the isolated region may be maintained within a predetermined range by, e.g., adding and/or removing fluid, including any of the chemotherapeutic agents described herein, from one or more openings in the apparatus between the occluders.

Any of the apparatuses described herein may include a lumen for a wire (e.g., guidewire) so that the apparatus may be delivered over the guidewire. The wire lumen may include a lubricious material, such as a coating or sleeve of lubricious material, etc. For example, any of these apparatuses may include a lubricious liner in the wire lumen. In some examples the apparatus may be configured as a rapid exchange and/or monorail apparatus, including a rapid exchange wire channel region at the distal end region of the apparatus. The rapid exchange region may be distal to the occluders or it may span the occluders.

These apparatuses may include one or more structural reinforcements, such as braids, coils, etc. on all or a portion of the apparatus. For example, the occluders may include a reinforced region. The catheter forming the apparatus may be reinforced (e.g., the catheter extrusion may be a reinforced catheter extrusion, including a braid, coil, etc.).

Any of these apparatuses may include one or more markers for visualizing the position of the apparatus within the body. For example, the apparatus may include one or more radiopaque markers for visualizing the apparatus during insertion, operation and/or removal of the apparatus. In some examples the one or more radiopaque markers may be positioned on or adjacent to each of the occluders, which may provide an indication of the position and span of the isolated region of the lumen. One or more markers may be positioned outside of this region (e.g., a third marker may be fixed proximal to the proximal occluder). The marker may include markers for any appropriate visualization, including radiopaque (e.g., fluoroscopic imaging), ultrasound markers (ultrasonic imaging), etc.

In some examples, the method of isolating the region of the lumen may include a method of isolating a region of the lumen including or adjacent to a bifurcation. For example, in some examples the method may include expanding an occluder within a bifurcated region of the lumen, an occluder sufficiently conformal to occlude at a bifurcation, a bifurcated occluder that can individually occlude each branch of a bifurcation, or two or more independent occluders to occlude each branch of a bifurcation (and other branch vessels, as needed).

Other objects of the invention may be apparent to one skilled in the art upon reading the following specification and claims. All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

Figure 1:
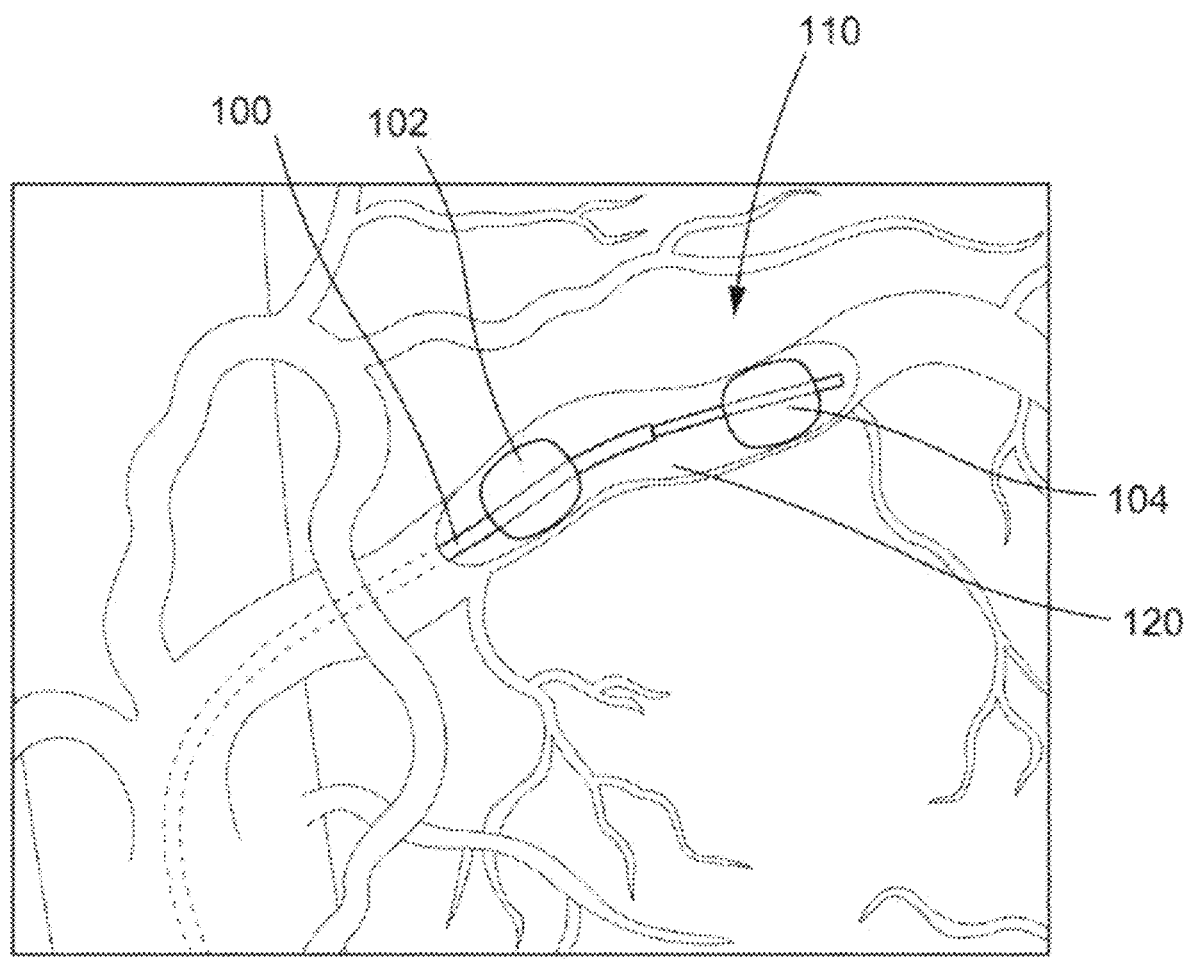
FIG. 1 is an illustration of a catheter device disposed within a vessel, according to an embodiment.

This disclosure is not limited to particular methodologies or the specific compositions described. It is also understood that the terminology used herein is for the purpose of describing particular embodiments only, and is not intended to be limiting, since the scope of the present application will be limited only by the appended claims and their equivalents.

Unless defined otherwise, technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described.

As used herein and in the appended claims, the singular forms "a," "and," and "the," include plural referents unless the context clearly dictates otherwise. Thus, for example, the term "chemotherapeutic" is intended to mean a single chemotherapeutic or a combination of chemotherapeutics; "a course of radiation therapy" is intended to mean one or more courses of radiation therapies, or combinations thereof; the term "agent" is intended to mean a single agent or a combination of agents, and so on and so forth.

As utilized in accordance with the present disclosure, the following terms, unless otherwise indicated, shall be understood to have the following meanings:

The words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

"Treat", "treating" and "treatment" of cancerous tumors refer to reducing the frequency of symptoms of cancer (including eliminating them entirely), avoiding the occurrence of cancer, and/or reducing the severity of symptoms of cancer.

"Therapeutically effective amount" and "therapeutically effective dose" means the amount or dosage of a compound that, when administered to a patient for treating cancerous tumors, is sufficient to effect such treatment. The "therapeutically effective amount" or "therapeutically effective dose" will vary depending on, for example, the compound, the size of the tumor, and the age, weight, etc., of the patient to be treated.

Described herein are methods for treating or ameliorating solid tumors (including cancerous tumors), by first reducing, inhibiting or suppressing the microvasculature around one or more tumors or between a lumen of a body (e.g., artery, vein, or any other both lumen) and the tumor(s), then, once the microvasculature has been compromised, e.g., inhibited, reduced or suppressed, isolating a region ("segment") of the lumen of the body, e.g., by occluding the end of the segment, and applying one or more chemotherapeutic agent into the segment under pressure so that it may be effectively delivered to the one or more tumors, without disrupting the tissue unduly and with little or reduced washout. For example, the microvasculature may be inhibited, reduced or suppressed by the application of a course of targeted radiation therapy that is first administered to an area including one or more tumors ("target tissue region"). A period of time may be allowed to elapse in order for the radiation to take effect in down-sizing the tumor(s) and/or inhibiting, reducing or suppressing the microvasculature in the tissue of the tumor and/or the tissue around the tumor. The radiation may reduce the microvasculature in the tissue in the area including the tumor(s). This period may be followed by the administration of a therapeutically effective amount of a chemotherapeutic agent to an isolated section of the lumen near the solid tumor. In some examples, the lumen may be an artery. Isolation of the section (e.g., arterial section) may be accomplished by isolating the proximal and the distal part of the vasculature closest to the tumor whereby the intraluminal pressure may then be decreased to the level of the interstitium. The therapeutically effective dose of the chemotherapeutic agent may then be administered via infusion. Thus, in some examples, a combination of radiation therapy followed by properly administered chemotherapy is complementary and has a synergistic clinical effect when combined.

Although intra-arterial delivery of chemotherapy, including TAC and TACE, has been shown to be effective and safe in treatment of certain solid tumors, a prerequisite for effective TAC or TACE is the selective engagement of nearby arterial vessels and, more commonly, the vessels feeding the tumor itself. The precise engagement of the feeding or branch vessel remains a major limitation for expanding the use of TACE and TAC in solid tumors, including but not limited to, pancreatic adenocarcinoma. The isolation of the artery supplying the tumor or the relevant tissue can be a technical challenge for a number of reasons, for example: a) there are organs with no dedicated single blood vessel supplying those specific organs; b) side and terminal branches of an artery can cause collateral flow to tissues and organs beyond the area of interest; and c) the tumor feeder vessels may be too small for detection by angiography; and d) the feeding branch/artery cannot be cannulated.

To address these problems, methods disclosed herein may involve administering a therapy to reduce the microvasculature in the region of the tissue between an adjacent lumen and the tumor(s), such as (but not limited to) radiation therapy. Thus, the therapy, e.g., radiation, may reduce the microvasculature in the area including the tumor. After the therapy, the proximal and the distal part of the lumen (e.g., the vasculature such as an artery, vein, or other body lumen, such as a trachea, urethra, fallopian tube, esophagus, etc.) closest to the tumor(s) is isolated using an apparatus having two or more occluders, such as a double balloon catheter. Both the side and the terminal branches may be excluded, which prevents drug washout. The reduced microvasculature in the tissue in the area also reduces drug washout. Upon expanding the occluders, e.g., by inflation of both balloons, in the isolated luminal segment, the intra-luminal pressure may be reduced to the level of interstitium (typically, about 10-20 mmHg). A therapeutic agent such as, for example, a chemotherapeutic drug, can be infused into the isolated arterial segment. The infusion of the chemotherapeutic drug in the isolated region, without any major runoff, leads to an increase in the intra-luminal pressure of at least about 30 mmHg in the isolated luminal segment. The pressure gradient forces the infused agent to traverse the lumina (e.g., arterial) wall and enter the surrounding tissue. When the lumen is an artery, the infused agent may traverse the vasa vasorum surrounding the vessel wall, with subsequent influx of the therapeutic agent into the tissue. Although the method is not limited to arteries, but may be used with virtually any lumen, for convenience, this technique is referred to herein as "trans-arterial microperfusion" or TAMP.

According to certain embodiments described herein, TAMP is not dependent on angiographic identification and cannulization of the tumor arterial supply or feeding vessels and thus overcomes deficiencies of current techniques. In TAMP, the drug traverses the luminal wall (e.g., in arteries, endothelium and media) before entering into the adventitia and interstitium. The interstitial concentration achieved is dependent on both the influx of the drug into the tissue across the artery wall and the efflux of the drug out of the interstitium via capillaries in the tissue area and the venous system. Hence, one can increase localized tissue concentration by both increasing the influx and reducing the efflux using the approach described above. The infusion parameters that determine the influx of the drug via TAMP include, but are not limited to, the intraluminal pressure achieved between the occluders (e.g., in some examples, balloons), the intraluminal drug concentration, and the duration of infusion. By varying these parameters, one can change the drug influx and interstitial concentration.

In some embodiments, catheter devices such as those described in U.S. patent application Ser. No. 14/293,603, filed Jun. 2, 2014, titled "Devices, methods and kits for delivery of therapeutic materials to a target artery," now issued as U.S. Pat. No. 9,457,171, and U.S. patent application Ser. No. 14/958,428, filed Dec. 3, 2015, titled "Occlusion catheter system and methods of use," the disclosures of which are incorporated herein by reference, can be used and/or adapted for use with TAMP techniques described herein. FIG. 1 depicts an example of an apparatus, configured as a catheter device 100. The catheter device 100 includes a first occluder 102 and a second occluder 104. The occluders 102, 104 can be any suitable devices or mechanisms that are configured to selectively limit, block, obstruct, seal, or otherwise occlude a bodily lumen (e.g., artery) in which the occluders 102, 104 are disposed. For example, in some embodiments, the occluders 102, 104 can be inflatable balloons or the like that can be transitioned between a collapsed (e.g., deflated) configuration and an expanded (e.g., inflated) configuration. The first occluder 102 can be coupled to a distal end portion of a first catheter, and the second occluder 104 can be coupled to the distal end portion of a second catheter. Alternatively, in some embodiments, the first occluder 102 and the second occluder 104 can be coupled to a single catheter at different points along the catheter. The catheter device 100 can be used to isolate a segment 120 of a bodily lumen (e.g., artery) within the space defined between the first occluder 102 and the second occluder 104. After the segment 120 is isolated, a procedure can be performed within the isolated segment 120 such as, for example, delivering a therapeutic agent to the isolated segment 120 and surrounding tissue 110.

Figure 2:
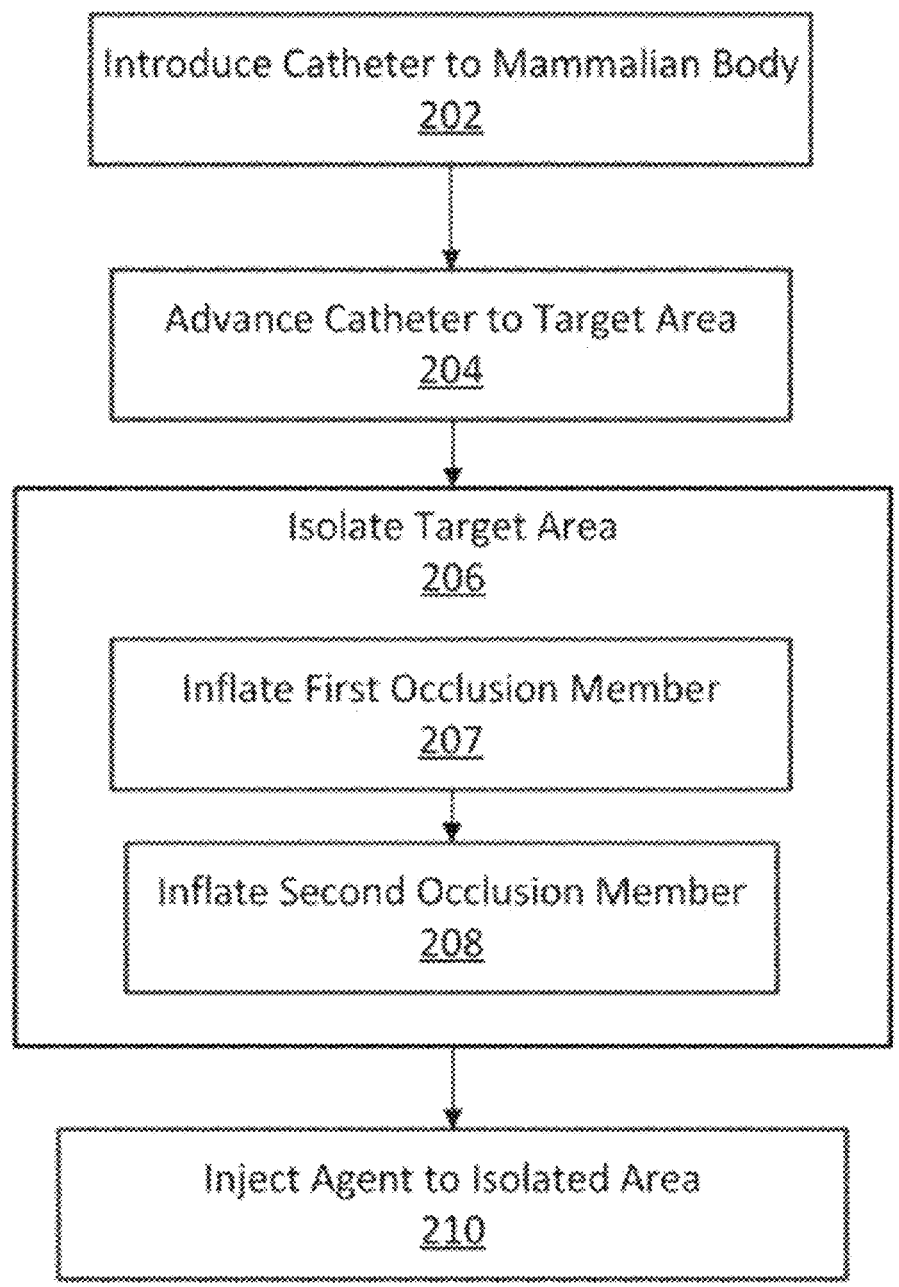
FIG. 2 is a flowchart illustrating a method for treating a cancerous tumor, according to embodiments described herein.

FIG. 2 illustrates an example of a method 200 for performing a TAMP procedure. The method includes introducing a catheter (e.g., the catheter device 100) into a mammalian body into a bodily lumen (e.g., artery), at 202. The catheter can be advanced to a target area, at 204, and used to isolate the target area, at 206. In some embodiments, the catheter can include two occluders (e.g., occluders 102, 104) that can be deployed (e.g., inflated) to isolate a segment of the bodily lumen to exclude the segment from its side and terminal branches. For example, a first occluder (e.g., a distal occluder) can be inflated, at 207, and a second occluder can be inflated (e.g., a proximal occluder), at 208. After the occluders are deployed, an agent can be injected through an injection port of the catheter device to the isolated segment disposed between the two occluders, at 210. In some embodiments, a contrast dye can be injected into the isolated segment and the surrounding area can be visualized to determine whether the segment has been correctly isolated. For example, the injection of contrast through the infusion port can ensure that no extra vessels or bodily lumens are included in the isolated area. If desired, the catheter can be moved, and the procedure repeated until the clinician can confirm that the catheter is correctly positioned. After the positioning of the catheter is confirmed, a therapeutic cell/biologic/agent can be introduced to the isolated segment through the infusion port.

Figure 3:
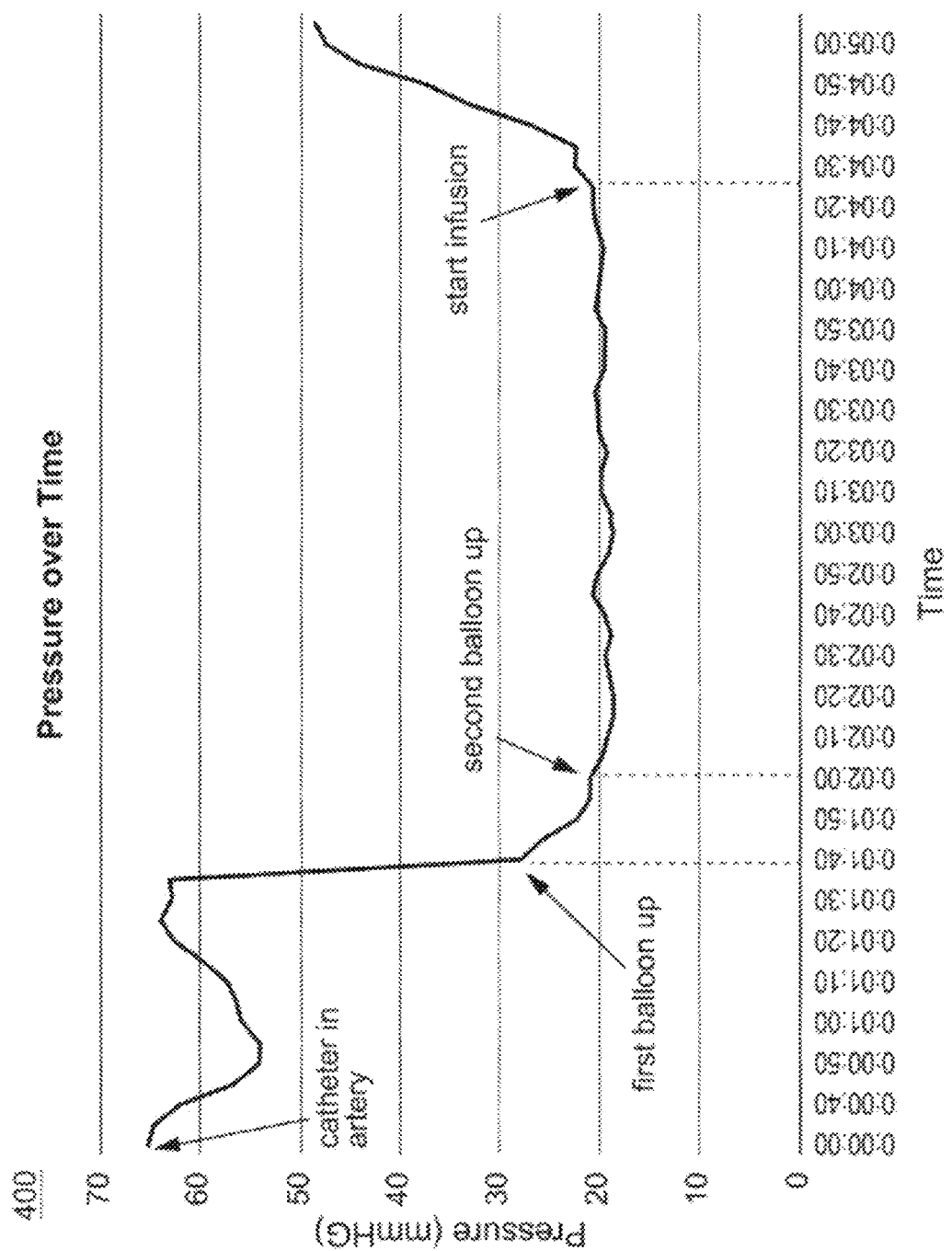
FIG. 3 is a graph showing a change in pressure (mmHg) in a vessel over time while undergoing treatment, according to an embodiment.

FIG. 3 graphically 400 illustrates how pressure (mmHg) in a bodily lumen (e.g., artery) changes over time as a TAMP procedure is performed (e.g., method 200). As shown in FIG. 3, the pressure in the bodily lumen drops when a first balloon (occluder) is inflated and continues to drop until a second balloon (second occluder) is inflated. The pressure then increases when an agent (e.g., a contrast dye, a therapeutic agent) is infused into the segment isolated by the first occluder (e.g., balloon) and the second occluder (e.g., balloon).

Figure 4A:
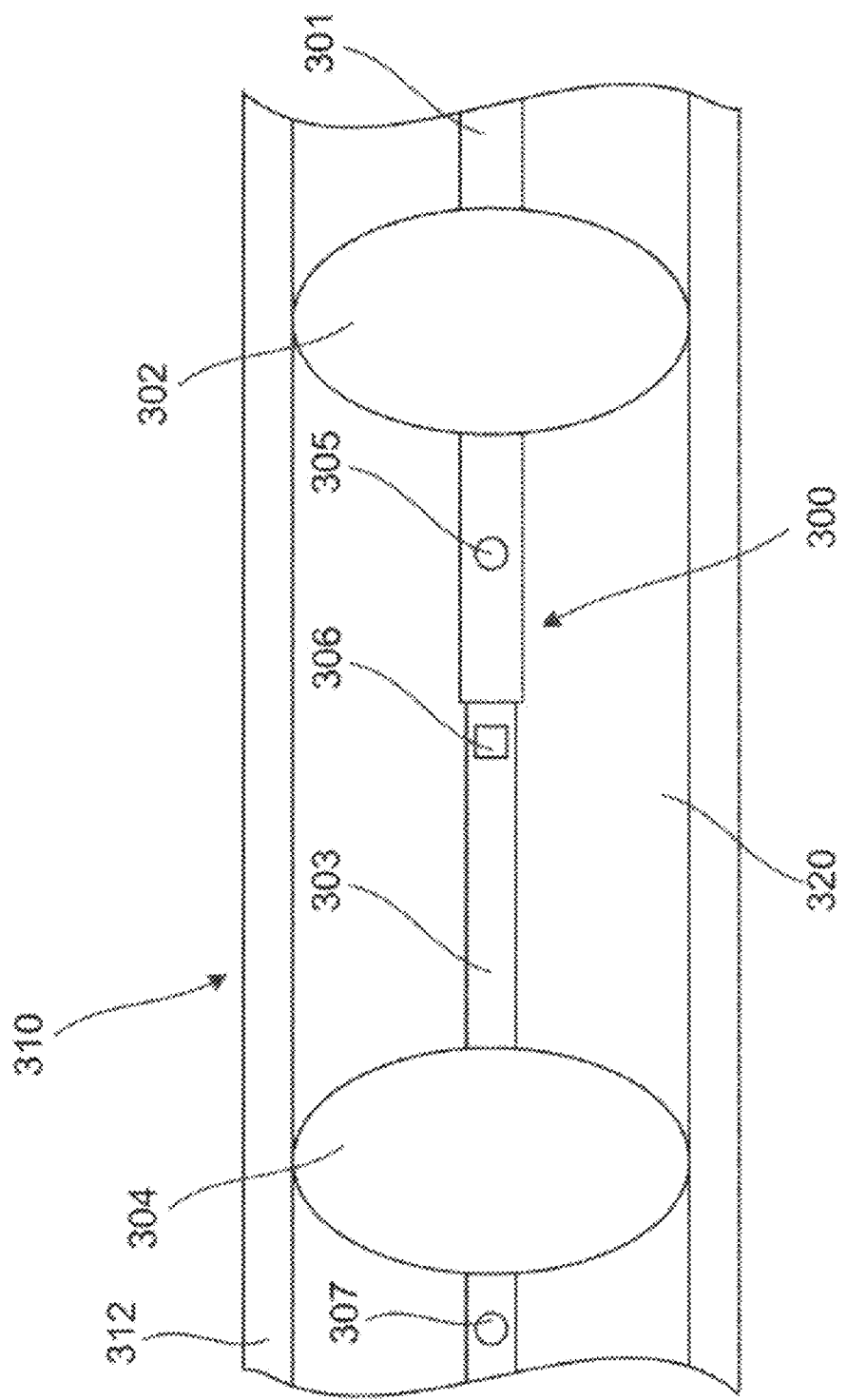
FIG. 4A is schematic illustration of a catheter device shown in a dilated configuration disposed within a vessel, according to an embodiment.
Figure 4B:
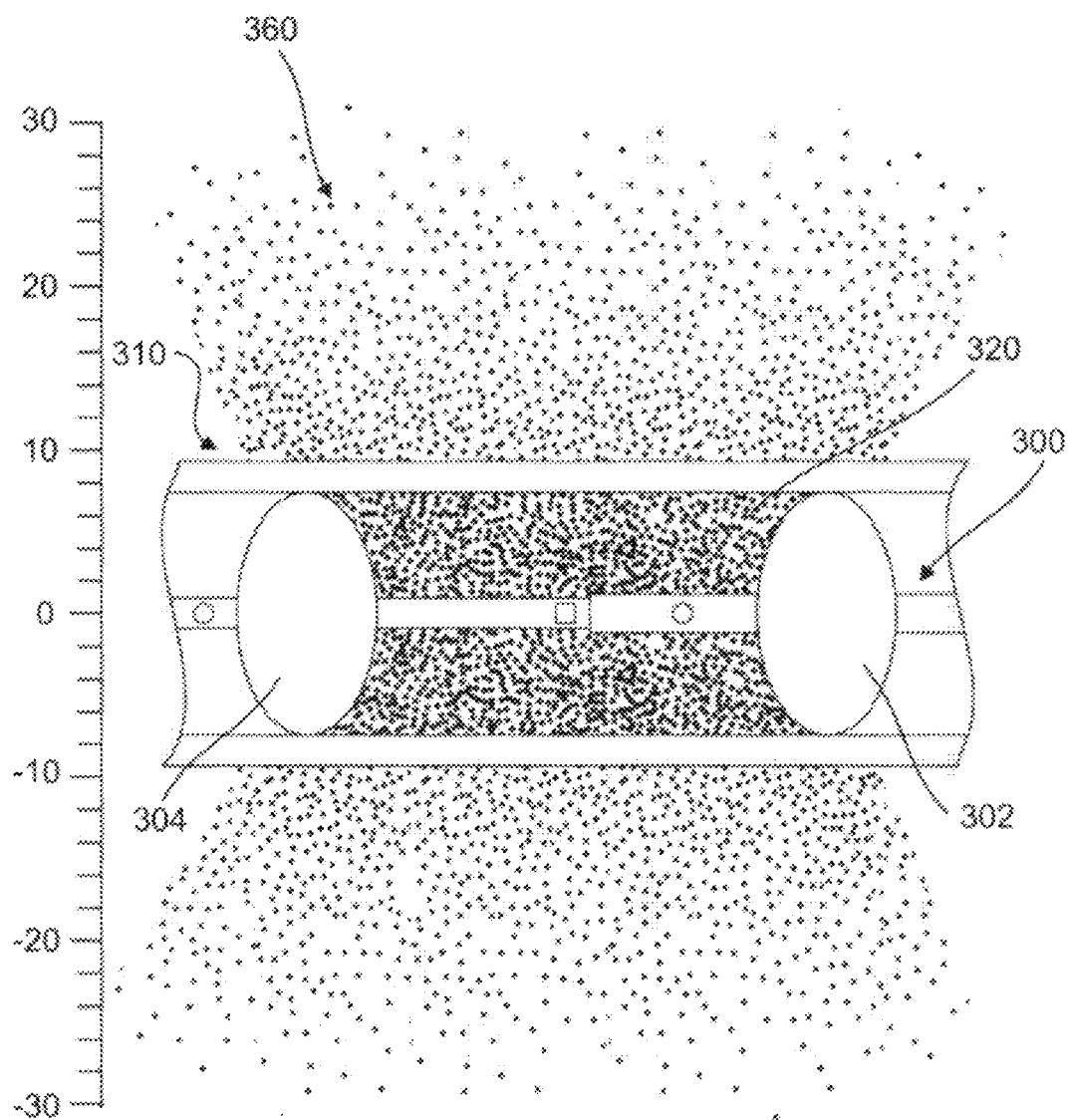
FIG. 4B is a schematic illustration of dispersal of an infused agent into tissue surrounding a vessel, according to an embodiment.

FIGS. 4A and 4B schematically depict an example of an apparatus, configured as a catheter device 300, disposed within a bodily lumen 310 (e.g., artery) and the dispersal of an infused agent 360 through the bodily lumen 310 into surrounding tissue. According to methods described herein (e.g., method 200), the infused agent 360 can be injected into an isolated segment 320 and allowed to infuse into the surrounding tissue via, for example, a concentration gradient. As shown in FIG. 4B, the infused agent 360 can infuse through a wall 312 of the bodily lumen 310 into the surrounding tissue. As shown, the concentration of the infused agent 360 decreases as the distance (shown in millimeters (mm)) from the isolated segment 320 of the bodily lumen 310 increases.

In combination with the techniques described above, if one can decrease the tissue efflux of the chemotherapeutic drug, the drug concentration near an isolated segment of a bodily lumen may be advantageously increased. When a tumor is located in this region, the increased concentration can increase the effect of the chemotherapeutic drug on the tumor. One technique that can decrease tissue efflux is to radiate the tissue prior to treatment. Radiation can decrease tissue microvasculature in tissue containing cancerous tumors. Thus, combining prior radiation to decrease tissue microvasculature with TAMP can have a synergistic effect. Combining the steps of radiation of the cancerous tissue prior to the treatment, waiting two or more weeks for the microvasculature to decrease, followed by use of the TAMP technique to deliver chemotherapy in the isolated segment of the bodily lumen (e.g., artery) closest to the tumor, produces a synergistic effect that the use of the TAMP technique alone does not.

Methods described herein can be used to treat solid cancerous tumors arising from any organ of the body where the tumor has its own or a proximate blood supply provided by a bodily lumen (e.g., artery) that can be isolated. Examples of cancers that can be treated using methods described herein can be, but are not limited to, pancreatic cancer, lung cancer, liver cancer, uterine cancer, colon cancer, or brain cancer.

For example, apparatuses and methods described herein can be used to isolate a targeted region in a patient's pancreas. Studies have shown that a course of radiation prior to TAMP treatment has significant clinical benefit in patients with locally advanced pancreatic cancer. Combining these two modalities led to a significant increase in median survival, a reduction of tumor markers, and downsizing of the tumor. A similar combination therapy administered by methods described herein may have clinical benefit in solid tumors in other organs and tissue areas where TAMP may be considered as a treatment option. Such tumors include, but are not limited to, pancreatic tumors, lung tumors, brain tumors, liver tumors, uterine tumors, and colon tumors. For example, when treating a lung rumor, these methods may include performing TAMP in an as described herein within the pulmonary artery. These methods may include performing TAMP in a gastro-duodenal artery. When treating the brain, the method may include performing TAMP in an internal carotid artery and/or anterior and/or middle cerebral arteries. In some examples TAMP may be performed in a vertebral artery.

In some embodiments, a method of treating a cancerous tumor can involve: first administering a course of radiation therapy targeting tissue including a solid cancerous tumor; second waiting a period of time for the destructive effect of the radiation on the vasculature to take effect; and third administering a therapeutically effective dose of a chemotherapeutic agent to an isolated section of a bodily lumen near the solid tumor. The targeted solid tumor can be, for example, a pancreatic tumor, a lung tumor, a brain tumor, a liver tumor, a uterine tumor, a colon tumor, or virtually any other type of tumor. The administration of radiation on the targeted tissue area can include, for example, delivering approximately 20 to 50 Gy of radiation over approximately one to five weeks in approximately one to 25 sessions. The period of time between administration of the radiation therapy and administration of the chemotherapeutic agent can be selected to maximize the devascularization of the tissue surrounding the tumor. Depending on various factors including the specific course of radiation and the specific tissue area or organ, this period of time can be, for example, approximately one to six months, as short as two weeks, or as long as six months. Examples of suitable chemotherapeutic agents include doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate or a combination of these drugs. In some embodiments, the section of the bodily lumen near the cancerous tumor can be isolated by the use of a catheter device to deliver the chemotherapeutic agent. In some embodiments, the catheter device can be used to increase the intraluminal pressure in the isolated section of the bodily lumen to achieve increased tissue penetration.

In some embodiments, a method of treating a cancerous tumor can involve: first administering a targeted dose of radiation to tissue including a solid tumor; second waiting a period of time; third isolating an area containing a cancerous tumor; and fourth administering a localized therapeutically effective dose of a chemotherapeutic agent. Similar to other methods described herein, the targeted solid tumor may be, for example, a pancreatic tumor, a lung tumor, a brain tumor, a liver tumor, a uterine tumor, or a colon tumor. The administration of radiation on the targeted tissue area can include, for example, delivering approximately 20 to 50 Gy of radiation over approximately one to five weeks in approximately one to 25 sessions. The period of time between administration of the radiation therapy and administration of the chemotherapeutic agent can be selected to maximize the devascularization of the tissue surrounding the tumor. Depending on various factors including the specific course of radiation and the specific tissue area or organ, this period of time can be, for example, at least a month. The isolated area can be, for example, an artery that is in proximity to the tumor. In some embodiments, a catheter device can be used to isolate the area. The catheter device can be used to increase the intraluminal pressure in the isolated artery. The isolated area can be, for example, the area of tissue involving the tumor. Examples of suitable chemotherapeutic agents include doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate or a combination of these drugs.

In some embodiments, a method of treating a cancerous tumor can involve: administering a course of radiation therapy to tissue including a solid tumor; isolating the proximal and the distal part of the vasculature closest to the tumor to produce an isolated arterial segment; decreasing the intraluminal pressure of the isolated arterial segment to the level of the interstitium; and administering a therapeutically effective dose of a chemotherapeutic drug. The course of the radiation therapy can decrease tissue efflux of the chemotherapeutic drug. In some embodiments, the vasculature can be isolated using a double balloon catheter positioned to exclude both the side and terminal branches of the artery. The chemotherapeutic drug can pass across the artery wall and into the surrounding tissue via a pressure gradient generated by the increase in the intraluminal pressure above the interstitial pressure. In some embodiments, the method can additionally include waiting a period of time following the step of administering the course of radiation therapy. The period of time between administration of the radiation therapy and administration of the chemotherapeutic agent can be selected to maximize the devascularization of the tissue surrounding the tumor. For example, depending on various factors including the specific course of administering the radiation therapy and the specific tissue region, this period of time can be at least two weeks. The targeted solid tumor can be, for example, a pancreatic tumor, a lung tumor, a brain tumor, a liver tumor, a uterine tumor, a colon tumor, or many other types of tumors. The chemotherapeutic drug can be, for example, a single chemotherapeutic or a combination of chemotherapeutic drugs.

Figure 5:
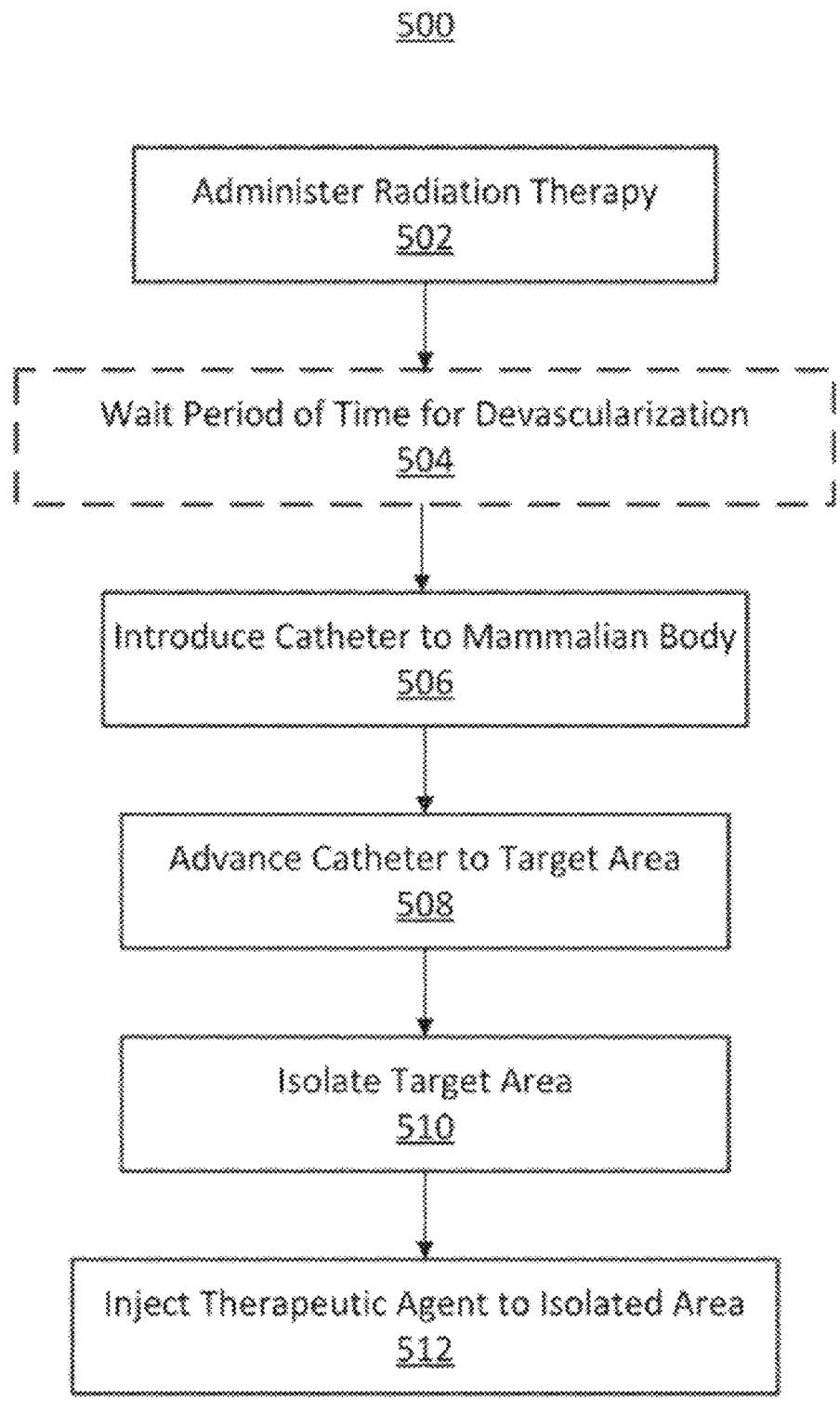
FIG. 5 is a flowchart illustrating a method for treating a cancerous tumor, according to embodiments described herein.

FIG. 5 is a flowchart illustrating a method 500 of treating a tumor involving the use of radiation. In particular, the method involves administering a course of radiation therapy to a target area, at 502. For example, an amount of radiation (e.g., 20-50 Gy) can be administered to a patient in multiple sessions (e.g. 1-25 sessions) over a period of time (e.g., a few days to six months). The target area can be a tissue area including a tumor. The method then optionally includes waiting a period of time for the radiation therapy to devascularize the tissue in the target area, at 504, e.g., to reduce the microvasculature in the region between a body lumen and the tumor.

The method 500 further includes introducing a catheter (e.g., the catheter device 100) into a mammalian body into a bodily lumen (e.g., artery), at 506. The catheter can be advanced to a target area, at 508, and used to isolate the target area, at 510. In some embodiments, the catheter can include two occlusion members (e.g., occluders 102, 104) that can be deployed (e.g., inflated) to isolate a segment of the bodily lumen to exclude the segment from its side and terminal branches. After the occluders are deployed, an agent can be injected through an injection port of the catheter device to the isolated segment disposed between the two occluders, at 512. In some embodiments, a contrast dye can be injected into the isolated segment and the surrounding area can be visualized to determine whether the segment has been correctly isolated. For example, the injection of contrast through the infusion port can ensure that no extra vessels or bodily lumens are included in the isolated area. If desired, the catheter can be moved and the procedure repeated until the clinician can confirm that the catheter is correctly positioned. After the positioning of the catheter is confirmed, a therapeutic cell/biologic/agent can be introduced to the isolated segment through the infusion port.

In some embodiments, the step of administering the radiation therapy (502) can occur during and/or after the steps of introducing the catheter into the mammalian body (506), advancing the catheter to the target area (508), isolating the target area (510), and/or injecting a therapeutic agent into the target area (512). In some embodiments, one or more steps of the method 500 can be repeated before, during, and/or after other steps of the method 500.

Figure 6A:
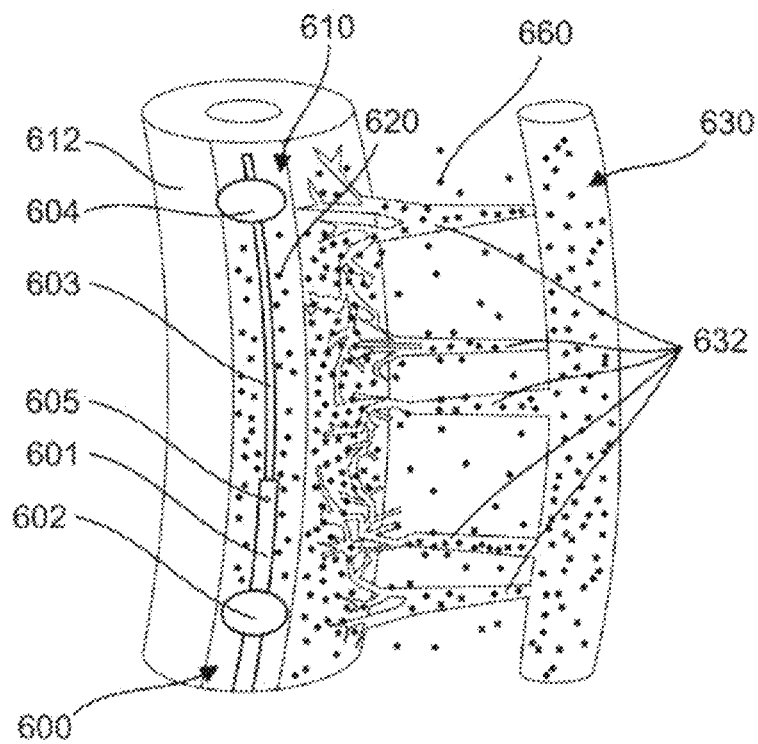
FIG. 6A is an illustration of dispersal of an infused agent into tissue surrounding a vessel without application of radiation therapy.
Figure 6B:
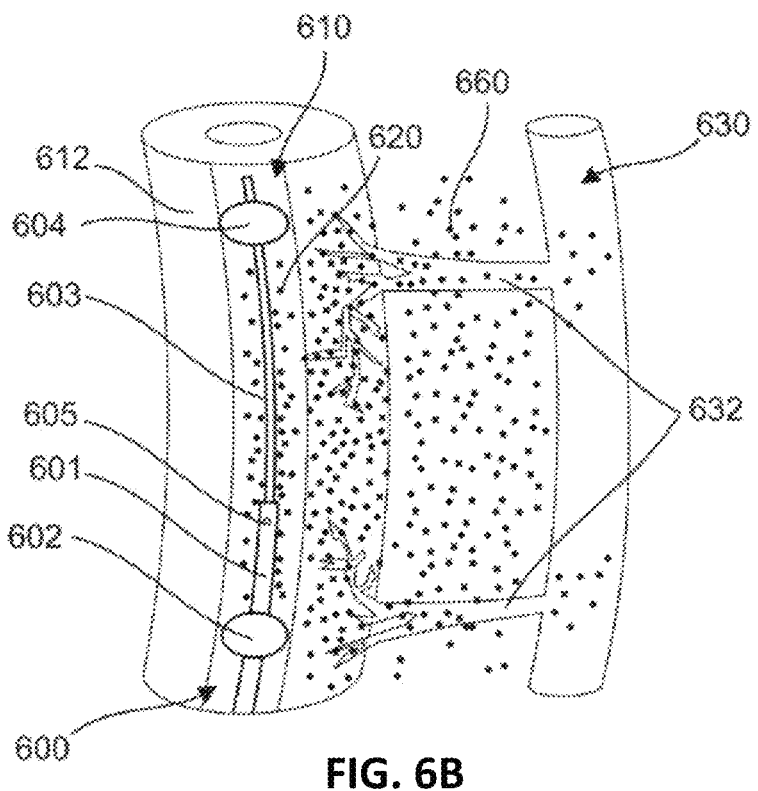
FIG. 6B is an illustration of dispersal of an infused agent into tissue surrounding a vessel with application of radiation therapy, according to embodiments described herein.

FIGS. 6A and 6B schematically illustrate the effects of radiation on the vasa vasorum microvasculature in tissue surrounding an isolated segment 620 of a bodily lumen 610. By reducing the microvasculature, the radiation therapy reduces drug washout and increases drug tissue concentration when a drug is delivered to the area using methods described herein, such as, for example, TAMP. FIG. 6A depicts an area of tissue surrounding an isolated segment 620 of a bodily lumen 610 prior to radiation therapy. FIG. 6B depicts the area of tissue after radiation therapy. After the radiation, the number of microvasculature connections 632 (e.g., micro-vessels extending from the isolated section 620 to the venous system 630) is reduced, thereby allowing a greater concentration of an infused drug 660 to remain in the tissue area.

As depicted in FIGS. 6A and 6B, a catheter device 600 can be used to deliver the infused drug 660 to the target area. The catheter device 600 can be similar to other catheter devices described herein (e.g., catheter device 100 and catheter device 300). For example, the catheter device 600 has a first occluder 602 and a second occluder 604, which are coupled to distal end portions of a first catheter 601 and a second catheter 603, respectively. The catheter device 600 also includes a port 605 for delivering the infused drug 660 to the isolated segment 620 between the first occluder 602 and the second occluder 604. Once the infused drug 660 is delivered to the isolated segment 620, it can pass through a wall 612 of the bodily lumen 610 into surrounding tissue.

Radiation Therapy

In methods described herein, radiation therapy can include, for example, external-beam radiation therapy delivered by X-rays, gamma rays, proton beams, or other appropriate sources. Radiation therapy damages cells by destroying the genetic material that controls how cells grow and divide. While both healthy and cancerous cells are damaged by radiation therapy, the goal of radiation therapy is to destroy as few normal, healthy cells as possible. The radiation therapy described herein can be targeted as narrowly as possible to the solid tumor(s) being treated or the tissue closely surrounding the solid tumor(s).

Typically, a radiation treatment plan is individualized for a patient, based upon detailed imaging scans showing the location of a patient's tumor(s) and the normal areas around it. The amount of radiation that normal tissue in different parts of the body can safely receive is known to one skilled in the art. Computed tomography (CT) scans are most frequently employed, but magnetic resonance imaging (MRI), positron emission tomography (PET), and ultrasound scans may also be used. A radiation oncologist determines the exact area that will be treated, the total radiation dose that will be delivered to the tumor, how much dose will be allowed for the normal tissues around the tumor, and the safest angles (paths) for radiation delivery. Radiation doses for cancer treatment are measured in Gy, which is a measure of the amount of radiation energy absorbed by one kilogram of human tissue. Different doses of radiation are needed to kill different types of cancer cells. Patients can receive external-beam radiation therapy in daily treatment sessions over the course of several weeks. The number of treatment sessions depends on many factors, including the total radiation dose that will be given. For example, one dose, which constitutes a fraction of the total planned dose of radiation, can be given each day. In a different instance, two treatments a day can be given.

As will be appreciated by one skilled in the art, the course of radiation therapy appropriate for use in the method of the present invention will depend on the specific cancerous tumor being treated. The specific dose of radiation, the duration of the radiation, and the number of treatments for any particular individual will depend upon a variety of factors including the type of cancer, the size of the tumor(s), and the patient's age and medical history including, for example, the amount of radiation previously received. Concurrent chemotherapy may also impact the dose of radiation given.

When treating a pancreatic cancer, for example, the course of radiation therapy can be approximately 20 to 50 Gy of radiation delivered in approximately one to 25 treatments over approximately one to five weeks. Alternatively, two to five sessions of radiation can be given over a period of approximately a week. For certain types of cancer, the amount of radiation therapy delivered may be as low as one Gy. In preferred embodiments, the course of radiation therapy can be approximately 40 to 50 Gy of radiation delivered in approximately 22 to 25 treatments over approximately four to five weeks. As may be appreciated by one skilled in the art, the amount of radiation therapy useful in methods described herein is that necessary to devascularize the solid tumor of interest thus allowing the TAMP technique to be used advantageously.

In methods described herein, after administering the radiation therapy, a physician may wait for a period of time before administering chemotherapy such that the tumorous tissue can die (e.g., necrosis) or become devascularized. In some embodiments, this period of time can be selected to maximize devascularization of the solid tumor and/or tissue containing the solid tumor. In some embodiments, this period of time can be selected to maximize the effect of the chemotherapy based on a sufficient amount of devascularization. In certain instances, the time period that elapses before administering chemotherapy can be at least a month. In other instances, the period of time is approximately two weeks to six months.

Chemotherapeutics

Specific chemotherapeutics can be selected based on the particular solid tumor that is to be treated. For example, the following chemotherapeutic agents and others may be used in the treatment of pancreatic cancer: doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate. In some embodiments, a combination of agents may be employed. For example, when treating pancreatic cancer, a combination of gemcitabine hydrochloride (Gemzar®) and paclitaxel albumin-stabilized nanoparticle formulation (Abraxane®) may be used.

In general, any appropriate chemotherapeutic agent may be used, including, but not limited to small molecule chemotherapeutic agents, immunochemotherapeutic agents, stem cells, hormones, particles (nanoparticles, microparticles, etc.) and combinations of these. For example, in addition to those already described above, the chemotherapeutic agent may include one or more (including combinations) of: Paclitaxel, Abraxane, Everolimus, Erlotinib Hydrochloride, Fluorouracil, Irinotecan Hydrochloride, Olaparib, Mitomycin, Irinotecan Hydrochloride Liposome, Sunitinib Malate, Lanreotide Acetate, and Lutetium Lu 177-Dotatate. Examples of combinations include, but not limited to: Folfirinox (Leucovorin Calcium {Folinic Acic}-Fluorouracil-Irinotecan Hydrochloride-Oxaliplatin), Gemcitabine-Cisplatin, Gemcitabine-Oxaliplatin, and OFF (Oxaliplatin-Fluorouracil-Leucovorin Calcium {Folinic Acic}). Other chemotherapeutic agents may include one or more (including combinations) of: alkylating agents, Nitrosoureas, Antimetabolites, Anti-tumor antibiotics, Topoisomerase Inhibitors, Mitotic Inhibitors, Corticosteroids, All-trans-retinoic acid, Arsenic trioxide, Asparaginase, Eribulin, Hydroxyurea, Ixabepilone, Mitotane, Omacetaxine, Pegaspargase, Procarbazine, Romidepsin, Vorinostat, All-trans-retinoic acid, Cisplatin, Entrectinib, Larotrectinib Sulfate, Nitrosourea, Pembrolizumab, Temozolomide, Carmustine, Bevacizumab, Naxitamab, and Lomustine.

Other chemotherapeutic agents may include one or more (including combinations) of: tumor antigen, immunotherapy agents, immunomodulators (e.g., thalidomide, lenalidomide, pomalidomide, etc.), stem cells, radiotherapy particles, steroids, hormones, coagulants, sclerosing agents (e.g., doxycycline, thiotepa, bleomycin, minocycline, 5-fluorouracil, etc.), cross-linking agents, etc.

Any of the agents described above may be used in combination with each other and/or in combination with a contrast media for fluoroscopic visualization.

The above-described chemotherapeutic agents are available from a variety of sources licensed to provide such agents for human use. Generic formulations of non-proprietary chemotherapeutics are typically available from a variety of manufacturers. A list of these licensed suppliers is available from the U.S. Food and Drug Administration's "Approved Drug Products with Therapeutic Evaluations," commonly known as the "Orange Book" (http://www.accessdata.fda.gov/scripts/cder/ob/). Proprietary chemotherapeutics are typically available from one manufacturer, also identifiable in the Orange Book. For example, the corporate source for Gemzar® is Eli Lilly and Company (Indianapolis, Ind.) and Celgene Corporation (Summit, N.J.) supplies Abraxane®.

Methods described herein can use an amount of chemotherapeutic agent that is known to be therapeutically effective at treating a tumor. For example, the amount of chemotherapeutic agent that is used can be based on the Prescribing Information for a particular chemotherapeutic drug. A physician can adjust the amount of the chemotherapeutic agent to an amount that is appropriate for use with the TAMP techniques described herein.

In methods described herein, a therapeutic agent (e.g., chemotherapy drug) can be delivered via rapid infusion (e.g., injected directly into an artery over a period of minutes, intravenous infusion (e.g., through a drip or pump over a period of approximately 20 minutes to a few hours), or continuous infusion (e.g., through a continuation infusion pump over a period of weeks to months). The infusion of the drug into an isolated space increases the intraluminal or interior pressure of the vessel to above the interstitial pressure of the surrounding tissue and the pressure gradient forces the drug across a vessel wall and into the surrounding tissue.

Apparatuses

In some examples the apparatuses for use to perform the methods described (e.g., the TAMP methods) herein may include catheter devices or systems. In some examples, the methods described herein can use a catheter device such as, for example, a device including two or more occluders, in some examples a double occlusion balloon device, to isolate a segment of a bodily lumen (e.g., artery) and allow infusion of a therapeutic agent (e.g., chemotherapy drug) into the isolated segment between the occluders after they are inflated. For example, methods disclosed herein may use catheter devices such as those described in U.S. patent application Ser. No. 14/293,603, filed Jun. 2, 2014, titled "Devices, methods and kits for delivery of therapeutic materials to a target artery," now issued as U.S. Pat. No. 9,457,171, and U.S. patent application Ser. No. 14/958,428, filed Dec. 3, 2015, titled "Occlusion catheter system and methods of use," which are incorporated herein by reference. Briefly, a catheter device suitable for isolating a section of a bodily lumen near a solid tumor includes, but is not limited to, features and functions such as, for example: (1) selective isolation of the targeted portion of the portion of the artery for targeted delivery of the therapeutic agent to the solid tumor; (2) an infusion port allowing first, injection of contrast into the isolated segment to allow direct visualization of the origin of the branches of the artery supplying the cancerous tissue, and second, introduction of chemotherapeutic drugs; and (3) a self-contained assembly unit with easy retrieval after completion of the procedure. In one embodiment, the catheter device includes expandable occluders in the form of inflatable balloons that can be used to isolate a proximal and distal end of a bodily lumen of interest.

As illustrated above, in some examples, the apparatus may be adjusted so that the distance between the occluders may be adjusted (increased or decreased).

Methods described herein can include, for example, introducing an apparatus (e.g., a catheter device) into a lumen such as into a splenic artery of the pancreas, or other appropriate body lumen adjacent and/or in a target tumor. The apparatus can have, for example, two lumens—one for inflation/deployment of the balloons/occluding elements and a second for introduction of the infusate (e.g., therapeutic agent) to the space between the two balloons. The catheter can be advanced to a target portion of the splenic artery. A region of the target portion of the splenic artery is selectively isolated and the infusate is injected into the isolated region. In some embodiments, the method can include advancing at least a portion of the catheter device to an ostium of a celiac artery, its hepatic branch (and its branches), or if necessary, the superior mesenteric artery, depending on a patient's anatomy. In some embodiments, a contrast dye is injected into the isolated region to confirm exclusion of side branches before injecting the infusate.

In some embodiments, the apparatus can have one or more features to achieve a desired effect on a specific anatomy of tumors. For example, there may be: (1) a separate inflation lumen for the proximal and the distal occluders/balloons to allow different size occluders/balloons proximally and distally; (2) slidable catheters to allow the distance between the occluders/balloons to be adjusted; and (3) a sensor at the tip to monitor pressure in the isolated segment of the bodily lumen.

FIGS. 4A and 4B schematically depict an example of a catheter device 300 disposed within a bodily lumen 310 (e.g., artery) and the dispersal of an infused substance 360 through the bodily lumen 310 into surrounding tissue. The catheter device 300 can be similar to other catheter devices (e.g., catheter device 100) described herein. For example, catheter device 300 includes a first occluder 302 and a second occluder 304 for occluding a portion 320 of bodily lumen 310. The first occluder 302 is coupled to a distal end portion of a first catheter 301, and the second occluder 304 is coupled to a distal end portion of a second catheter 303. The occluders 302, 304 are filter elements that can be moved between a collapsed configuration for insertion of the catheter device 300 into a body of a patient (e.g., into an artery) and an expanded or dilated configuration, as shown in FIGS. 4A and 4B, for occluding a portion of a bodily lumen. The occluders 302, 304 when in the collapsed configuration have a smaller outer perimeter (or diameter) than when in the expanded configuration.

As depicted in FIGS. 4A and 4B, the catheter device 300 can be used to isolate a segment 320 of a bodily lumen 310 within the space defined between the first occluder 302 and the second occluder 304. The catheter device 300 can include a lumen in fluid communication with port or opening 305 for delivering an agent 360 (e.g., a dye or a chemotherapy drug) to the space between the first occluder 302 and the second occluder 304. The first catheter 301 can define the lumen and the opening 305. The opening 305 can be disposed on the distal end portion of the first catheter 301 distal to the first occluder 302. The second catheter 303 can be movably disposed within a lumen defined by the first catheter 301 such that the second catheter 303 can be moved relative to the first catheter 301 to move the second occluder 304 relative to the first occluder 302. According to some embodiments of the disclosure, the second occluder 304 can be moved toward the first occluder 302 to increase pressure within the isolated segment 320. The increased pressure can be used, for example, to drive delivery of the agent 360 through the wall 312 of the bodily lumen 310 and into the surrounding tissue.

In some embodiments, the catheter device 310 can have a sensor such as a pressure transducer 306 that may assist with achieving an optimal pressure within an occluded arterial segment for optimizing trans-arterial diffusion of an infused substance during a method of cancer treatment (e.g., a TAMP procedure). The pressure transducer 306 may be disposed along the catheter device 300 in the isolated arterial segment 320 (e.g., disposed between the first occluder 302 and the second occluder 304 (as depicted in FIGS. 4A and 4B)). The pressure transducer 306 can be disposed on one of the catheters 301, 303, or disposed on one of the occluders 302, 304. The pressure transducer 306 can be designed to measure an intraluminal pressure of the isolated segment 320. The pressure measurements may be used to adjust the intraluminal pressure of the isolated segment 320 to a predetermined or optimal pressure level. A physician may use the pressure measurements to determine a rate of infusing a drug or other therapeutic material into the isolated segment 320 in order to decrease or increase the intraluminal pressure of the isolated segment 320. For example, a physician can increase the rate of infusion of a drug to increase the intraluminal pressure of the isolated segment 320 above the pressure of tissue surrounding the isolated segment 320 (e.g., above the pressure of the interstitium) to create a pressure gradient between the intraluminal space and the surrounding tissue to increase permeation of the infused drug through the arterial wall and into the tissue. Additionally or alternatively, a physician can increase or decrease the intraluminal pressure of the isolated segment 320 by adjusting the position of the two occluders 302, 304 relative to one another (e.g., moving the two occluders 302, 304 closer or further apart from one another). A sensor 307 outside of the segment may be present distally or proximally.

Although the examples of the TAMP methods described above typically include accessing and isolating a portion of an artery, any of these methods and apparatuses may be used in other body lumen as well, including veins. In some cases it may be advantageous to access the target lumen through a shunt or graft that allows for easier re-access to the same target lumen for additional treatment cycles. Thus, alternatively or additionally, these methods and apparatuses may be used in a patient having an arteriovenous (A-V) shunt, which may be used as described herein. In some cases, the shunt may be fitted to a patient and may be used for providing access for delivery of the TAMP treatment as provided hereinto to a region proximal or within the tumor.

In general, the TAMP methods described herein may be used in any target tissue in order to treat a tumor. Specifically, the apparatus including two or more occluders may be used in any appropriate lumen within or adjacent to the target tissue. For example, the methods described herein may include using an apparatuses including two or more occluders for delivery of the therapeutic agent (e.g., chemotherapeutic) agent(s) may be used in a target artery such as, but not limited to: gastro-duodenal artery, pulmonary artery, proper hepatic or left or right hepatic artery, superior mesenteric artery, celiac artery, inferior vesical artery, middle rectal artery, internal pudendal artery, pulmonary artery, uterine artery, arteries of the bladder (e.g., superior vesical branch of the internal iliac artery, inferior vesical artery, vaginal artery, obturator and inferior gluteal arteries), mesenteric artery, iliac artery (and its sub-branches), and/or the internal carotid artery (and it's sub-branches). The methods described herein may also include using an apparatus including two or more occluders as described herein to deliver a therapeutic agent (e.g., a chemotherapeutic agent) in a target lumen such as, but not limited to: veins (or in some examples, a shunt coupled to a vein), a bronchial lumen, a lumen of the digestive tract (esophagus, stomach, duodenum, small intestine, colon, rectum, etc.), a lumen of the bile duct (e.g., cholangio and pancreas), urethral, fallopian tubes, etc.

Determination of Therapeutic Effectiveness

The efficacy of the methods of the present invention in the treatment of solid cancerous tumors can be evaluated in human clinical trials conducted under appropriate standards and ethical guidelines as set forth by the U.S. Food and Drug Administration (FDA). Such studies are conducted according to U.S. and International Standards of Good Clinical Practice. Typically, such trials are comparison trials, in that the method of the present invention is utilized in one cohort of patients, while one or more other cohorts receive alternative methods of treating the tumors. The alternative methods can include, for example, treatment with systemic chemotherapy alone.

A clinical trial for the treatment of cancerous tumors may have a primary objective of evaluating survival in patients who undergo radiation therapy followed by intra-arterial delivery of a chemotherapeutic agent to an isolated arterial section near the solid tumor after a suitable interval of time elapses. The second objective of such a trial is to assess tumor response by known imaging techniques at the primary site of application of the chemotherapeutic agent. In particular, the size of the tumor before and after treatment can be determined and evaluated across different treatment methods. In addition, the conversion rate from unresectable or borderline resectable to potentially resectable or resectable tumors can be determined. The results may be analyzed using standard statistical techniques known to those skilled in the art.

The following examples, including clinical studies, are offered by way of illustration and not by way of limitation.

Examples: Experiments with Pig Tissue

Figure 7:
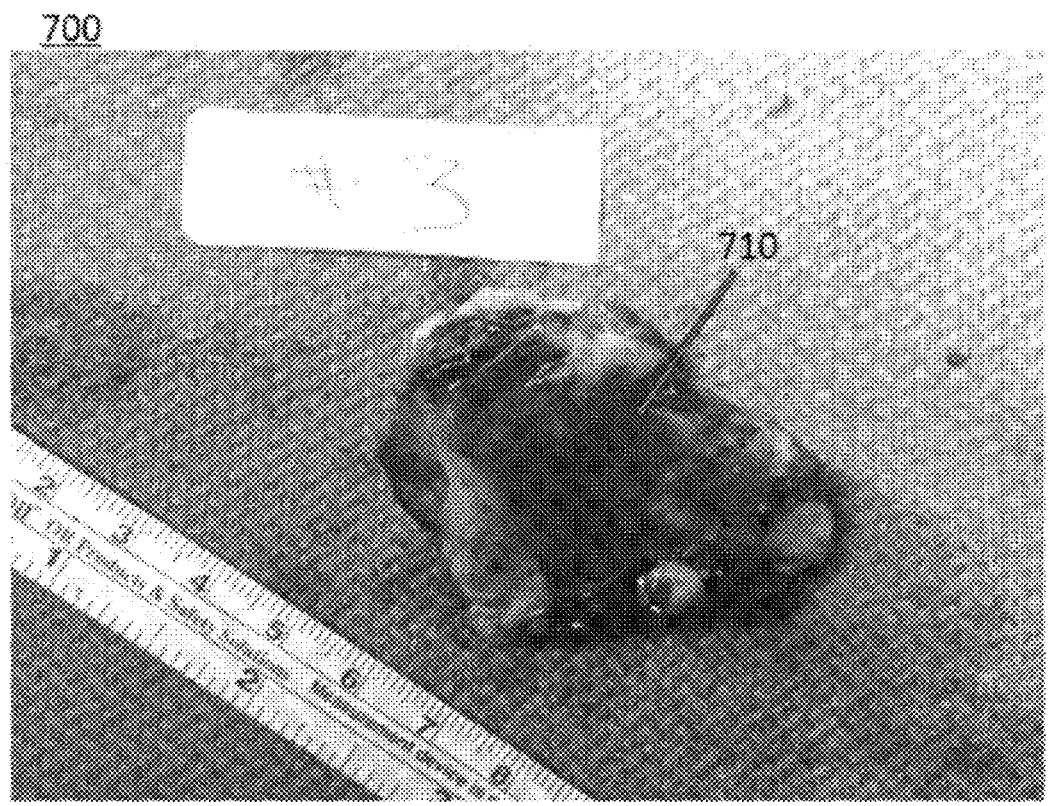
FIG. 7 is an image of a pancreatic tumor after undergoing treatment according to methods described herein.

FIG. 7 is an image 700 of a pancreatic tumor 710 of a pig after treatment with the TAMP method. The method involved occluding the celiac artery of the pig with a double balloon catheter, rapidly infusing dye at six milliliters per minute for ten minutes into the isolated segment of the celiac artery, and harvesting the tissue next to the celiac artery. As depicted, the infused dye has permeated into the harvested tissue.

Figure 8:
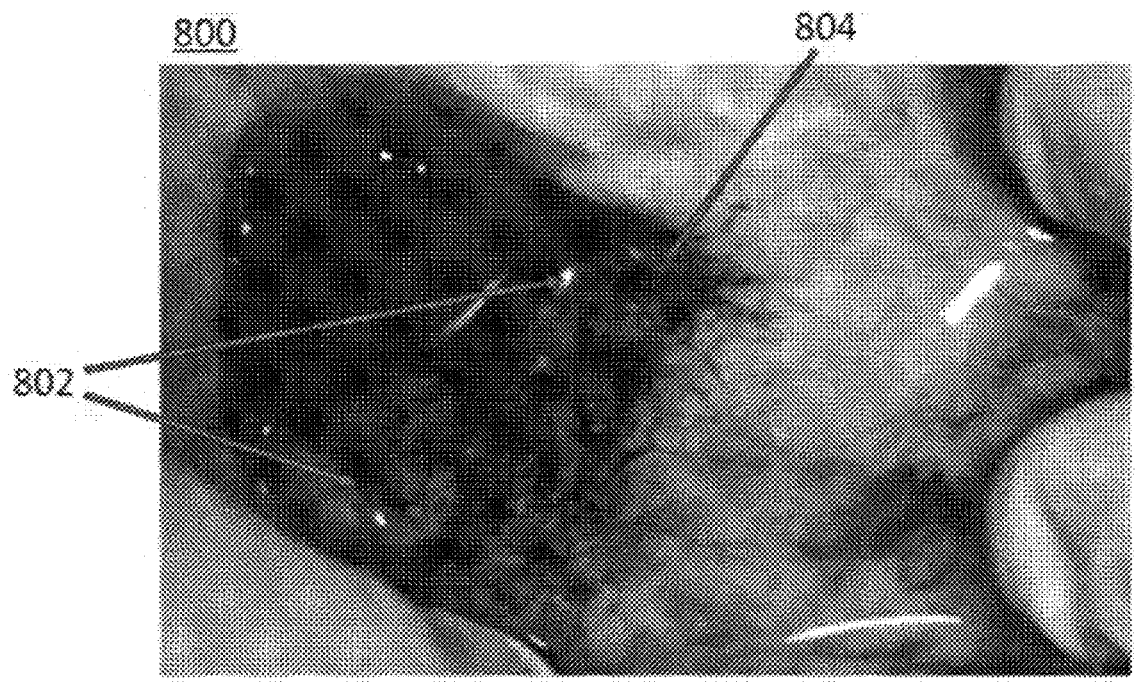
FIG. 8 is an image showing penetration of infused agents into tissue surrounding a vessel via the microvasculature, according to an embodiment.

FIG. 8 is an image 800 of tissue surrounding the celiac artery of a pig after treatment with the TAMP method. The method involved occluding the celiac artery of the pig with a double balloon catheter (i.e., a balloon catheter with occluders or balloons 802) and rapidly infusing dye at six milliliters per minute for ten minutes into the isolated segment of the celiac artery. The image shows the tissue surrounding the celiac artery in situ within ten sections after initiating the rapid infusion of the dye. As depicted in FIG. 8, the dye 804 has penetrated into the surrounding tissue via the vasa vasorum microvasculature.

Figure 11:
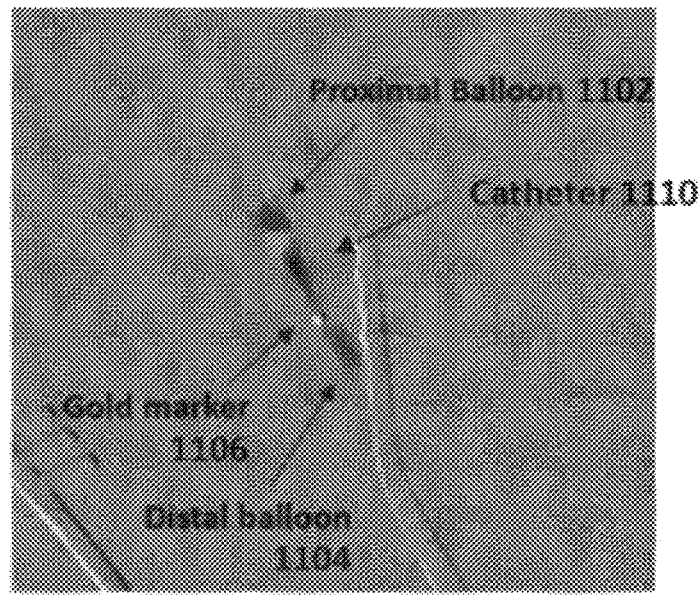
FIG. 11 is an image of a catheter device disposed in a vessel in a patient's groin area, according to an embodiment.
Figure 12:
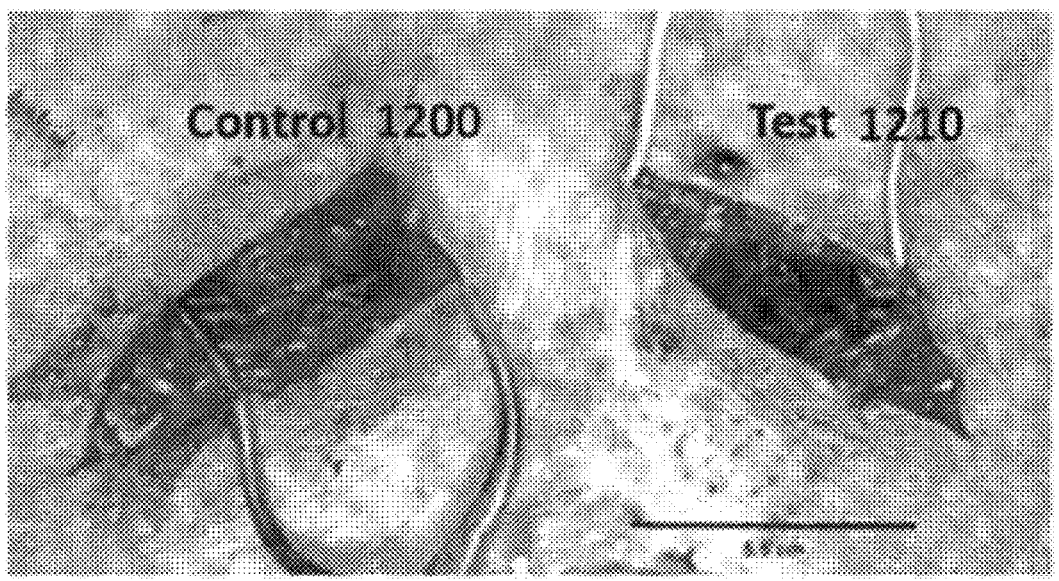
FIG. 12 is an image showing penetration of an infused agent into tissue surrounding a vessel after undergoing treatment, according to an embodiment.

FIGS. 11 and 12 relate to an experiment conducted on a pig to evaluate the effect of radiation on tissue penetration of drugs/molecules using the TAMP technique. The experiment involved administering radiation treatment to a left groin area in a pig and comparing the penetration of a dye introduced using the TAMP technique in the left groin area (referred to herein as the test 1200) versus the penetration of the dye in the right groin area (referred to herein as the control 1210). A Yucatan pig was anesthetized for a CT scan of the femoral artery to plan the radiation treatment. Both femoral arteries were accessed for the placement of sterile gold fiducial markers to mark the areas of interest for comparison following the radiation treatment and infusion of dye. The left groin area was treated with a single radiation session using the CyberKnife® system at 15 Gy outside the artery adjacent to the gold marker. FIG. 11 depicts an image 1100 of the left groin area with the gold marker 1106. One month following radiation treatment, with the animal under general anesthesia, a percutaneous exposure of the left and right femoral artery was completed. From the left carotid artery, a double balloon catheter 1110 was advanced to the area of the left femoral artery and a proximal balloon 1102 and a distal balloon 1104 of the catheter 1110 were positioned and inflated adjacent to the gold fiducial marker 1106, as shown in FIG. 11. The catheter 1110 isolated the relevant segment of the left femoral artery adjacent to the gold fiducial marker 1106 to ensure exclusion of any large side branches and to achieve optimal intravascular pressure in the isolated segment. A syringe pump was then used to inject a dye at six milliliters per minute for approximately 30 seconds through an infusion port between the two balloon catheters. The same procedure was repeated for the right femoral artery. At the conclusion of the procedures in the left and right femoral arteries, the area of dye penetration around the blood vessels were measured. As shown in FIG. 12, there was approximately a three-fold increase in penetration on the irradiated left side (i.e., test 1200) as compared to the control right side (i.e., control 1210).

Examples: Clinical Studies of Treating Pancreatic Cancer

A post-market registry study was conducted to assess patient survival and clinical outcomes using the RenovoCath™ RC120 catheter (RenovoRx, Los Altos, Calif.) in a clinical, prospective observational setting when used to deliver a chemotherapeutic to the pancreas as described in Table 1.

TABLE 1

| | |
|---|---|
| Study Title: | Inter-Arterial Treatment of Pancreatic Cancer Using the RenovoCath ™ RC120 Catheter |
| Development Phase: | Post market |
| Study Type: | Global Multicenter, Prospective, Observational Registry |
| Product Description: | The RenovoCath ™ RC120 Catheter is an endovascular multi-lumen, two handled catheter designed to isolate variable segments of arteries supplying the target organ using two slideable, compliant balloons. |
| Study Population: | Patients with pancreatic cancer, with and without prior radiation therapy |
| Chemotherapeutic agent: | Gemcitabine injection (Gemzar ®) |
| Primary Objectives | 1. Evaluate survival in patients diagnosed with pancreatic cancer who undergo intra-arterial delivery of chemotherapeutic agents to the pancreas<br>2. Assess tumor response in the primary site of application as assessed by imaging |
| Primary Endpoints | 1. Survival<br>2. Tumor response<br>3. Performance of RenovoCath in defined population (pancreatic cancer) in a clinical setting |
| Secondary Objective/ Endpoints | 1. Assess conversion rate from unresectable or borderline resectable to potentially resectable or resectable pancreatic cancer<br>2. Further define and analyze potential selection criteria for patients who present with locally advanced pancreatic cancer that may benefit from the intra-arterial procedure |
| Study Sites: | Multicenter |

After patient screening and enrollment, eligible patients underwent selective catheterization introduced via the femoral artery into the celiac axis into the splenic, hepatic and/or superior mesenteric artery(ies) using the TAMP technique as described above for the localized delivery of gemcitabine followed by embolization agent lipiodol. An interventional radiologist used the RenovoCath™ RC 120 catheter to optimize drug delivery to the tumor(s). At the conclusion of the case, the femoral artery arteriotomy was sealed and patient monitored as per standard institutional protocol.

All patients enrolled during the two-year registry enrollment period were followed periodically for survival outcome. Patients were contacted by telephone at the following intervals after the final intra-arterial treatment: 6 months±30 days, 1 year±30 days and 2 years±30 days. Patients were assessed for serious adverse events with specific attention to events related to local delivery of chemotherapeutic agents to the pancreas and device performance.

Figure 9:
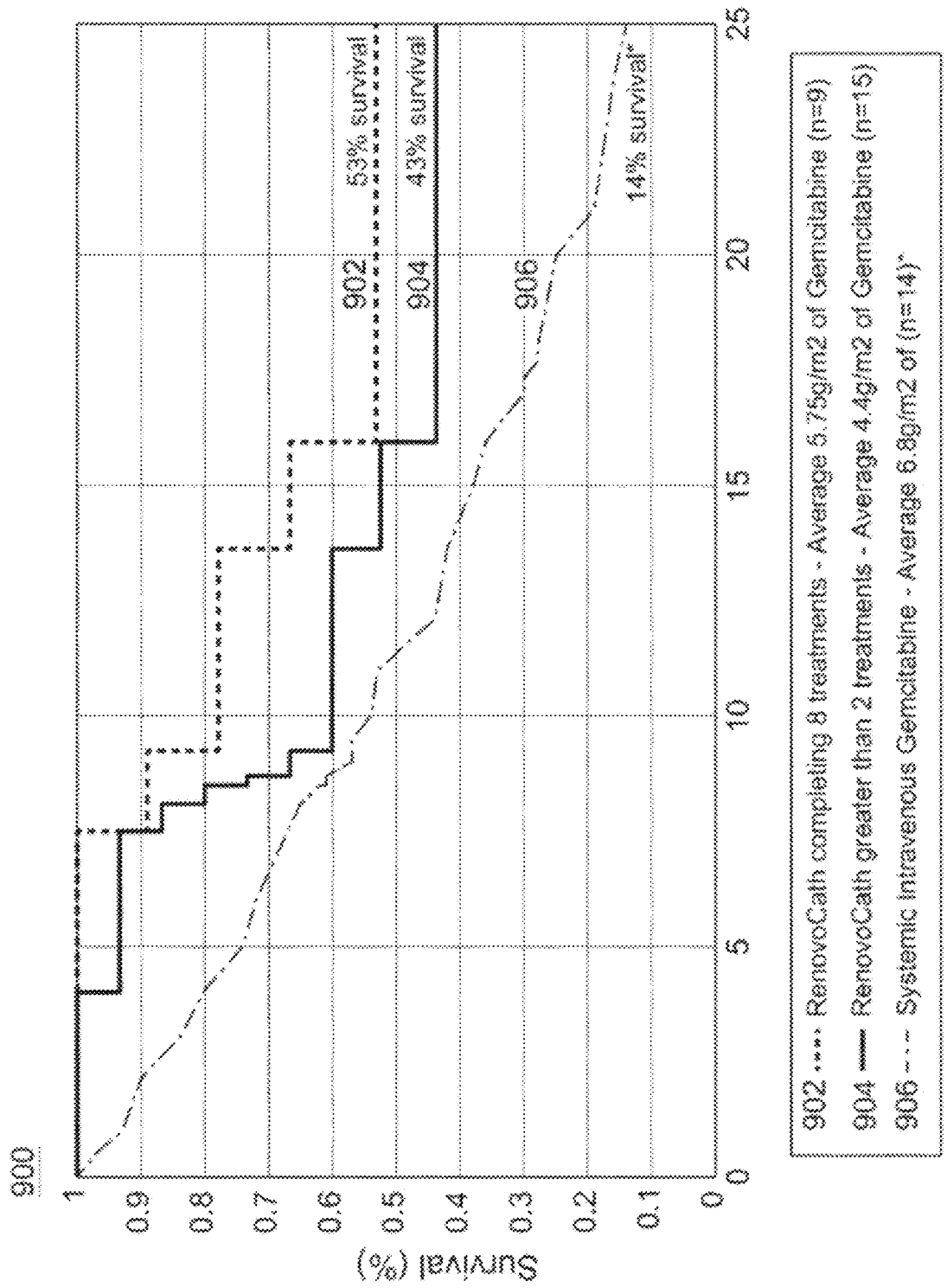
FIG. 9 is a graph comparing survival rates of patients treated according to different methods described herein.

FIG. 9 shows the superiority of the TAMP technique as compared to standard systemic chemotherapy. Graph 900 shows the increase in survival benefits in patients treated with TAMP compared to those treated with a systemic intravenous infusion of the same drug (i.e., gemcitabine). Line 902 represents the survival percentage of patients completing eight treatments of gemcitabine using the TAMP technique. Line 904 represents the survival percentage of patients completing more than two treatments of gemcitabine using the TAMP technique. And line 906 represents the survival percentage of patients given systemic infusion of gemcitabine, the results of which are taken from Chauffert et al., *Ann. Oncol.,* 2008, 19:1592-9. As depicted in FIG. 9, the survival rates of the patients treated with the TAMP technique (i.e., lines 902, 904) were greater than the survival rates of the patients given systemic infusion of the same drug (i.e., line 906).

Figure 10:
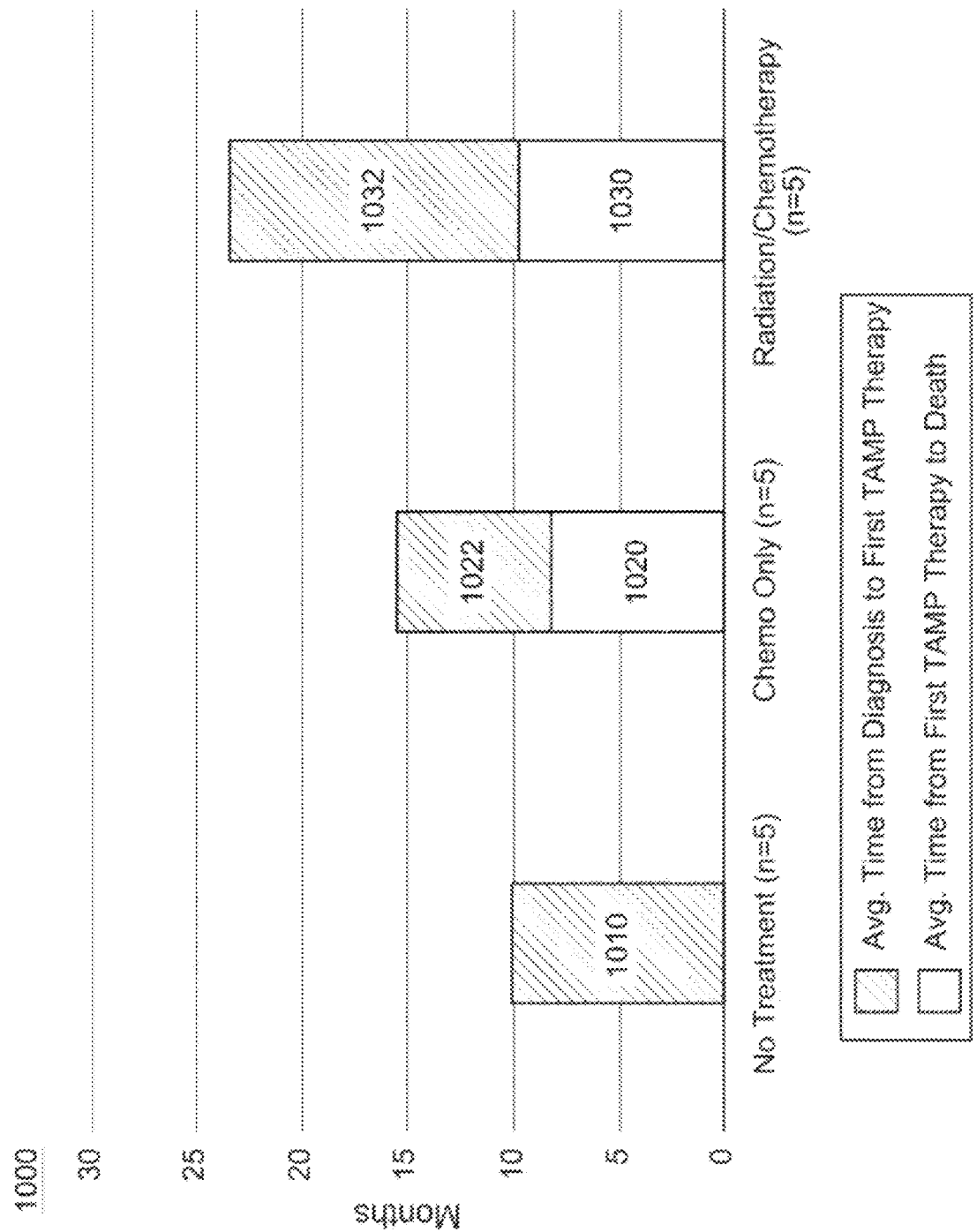
FIG. 10 is a bar chart comparing survival rates of patients treated according to different methods described herein.

FIG. 10 is a graph 1000 illustrating the effect of the TAMP technique on patient survival after radiation therapy compared with the effect of the TAMP technique with no radiation therapy. Fifteen patients with locally advanced pancreatic cancer were treated with gemcitabine in a dose-escalated protocol administered in four cycles using the TAMP technique. Each cycle consisted of two treatments two weeks apart. The efficacy data for the fifteen patients who received more than one cycle of TAMP treatment are shown in FIG. 6. Of these fifteen patients, five had no prior treatment of any kind, five had prior systemic chemotherapy, and five received radiation in additional to systemic chemotherapy prior to entering the study. On average, patients received radiation one to six months prior to enrolling in the study and receiving TAMP therapy. For the three groups of patients, the most pronounced survival benefit was seen in patients who had received radiation prior to the initiation of TAMP therapy. Specifically, patients with prior radiation had a significant improvement in survival compared to the ones that had either no prior treatment or only prior systemic chemotherapy with no radiation therapy. Patients were treated with TAMP therapy, regardless of their prior history. The dotted portion of the bars (1020, 1030) indicates the average time from diagnosis to the first TAMP therapy, while the clear portion of the bars (1010, 1022, 1032) indicates the average time from the first TAMP therapy to death.

This study demonstrated that a course of radiation prior to chemotherapy treatment administered via the TAMP technique has significant clinical benefit in patients with locally advanced pancreatic cancer. Combining these two modalities led to significant increase in median survival, reduction of tumor markers, and downsizing of the tumor. It is expected that a similar combination therapy would have clinical benefit in any solid tumors where diffusion-dependent infusion of a chemotherapeutic may be considered as a treatment option.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, pressure, flow, temperature, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, comprising:
   treating a target area including a tumor to reduce a microvasculature in the target area;
   inserting a catheter device into a lumen within or adjacent to the tumor, the catheter device including a first occluder and a second occluder;
   isolating a segment of the lumen proximate to the target area using the first occluder and the second occluder;
   delivering a dose of an agent to the target area having the reduced microvasculature from the isolated segment via the catheter device.

2. The method of claim 1, wherein inserting the catheter device into the lumen comprises inserting the catheter device into one of: a gastro-duodenal artery, a pulmonary artery, a proper hepatic artery, a left hepatic artery, a right hepatic artery, a superior mesenteric artery, a celiac artery, an inferior vesical artery, a middle rectal artery, an internal pudendal artery, a pulmonary artery, a uterine artery, a superior vesical branch of an internal iliac artery, an inferior vesical artery, a vaginal artery, an inferior gluteal artery, a mesenteric artery, an iliac artery and an internal carotid artery.

3. The method of claim 1, wherein inserting the catheter device into the lumen comprises inserting the catheter device into one of: a vein, a shunt coupled to a vein, a bronchial lumen, an esophagus, a stomach, a duodenum, a small intestine, a colon, a rectum, a bile duct, a urethra, and a fallopian tube.

4. The method of claim 1, wherein inserting the catheter device into the lumen comprises inserting the catheter device into a pulmonary artery.

5. The method of claim 1, wherein inserting the catheter device into the lumen comprises inserting the catheter device into an internal carotid artery or a common carotid artery.

6. The method of claim 1, wherein the agent is a chemotherapeutic agent.

7. The method of claim 6, wherein the chemotherapeutic agent includes one or more compounds selected from a group consisting of: doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, and sunitinab malate.

8. The method of claim 6, wherein the chemotherapeutic agent includes one or more of: Paclitaxel, Abraxane, Everolimus, Erlotinib Hydrochloride, Fluorouracil, Irinotecan Hydrochloride, Olaparib, Mitomycin, Irinotecan Hydrochloride Liposome, Sunitinib Malate, Lanreotide Acetate, and Lutetium Lu 177-Dotatate, Folfirinox (Leucovorin Calcium {Folinic Acic}-Fluorouracil-Irinotecan Hydrochloride-Oxaliplatin), Gemcitabine-Cisplatin, Gemcitabine-Oxaliplatin, and OFF (Oxaliplatin-Fluorouracil-Leucovorin Calcium {Folinic Acic}), an alkylating agent, a nitrosoureas, an antimetabolites, an anti-tumor antibiotic, a topoisomerase inhibitor, a mitotic inhibitor, a corticosteroids, an all-trans-retinoic acid, arsenic trioxide, asparaginase, eribulin, hydroxyurea, Ixabepilone, Mitotane, Omacetaxine, Pegaspargase, Procarbazine, Romidepsin, Vorinostat, Cisplatin, Entrectinib, Larotrectinib Sulfate, Nitrosourea, Pembrolizumab, Temozolomide, Carmustine, Bevacizumab, Naxitamab, and Lomustine.

9. The method of claim 6, wherein the chemotherapeutic agent includes one or more of: a tumor antigen, an immunotherapy agents, an immunomodulator, a stem cell, a radiotherapy particle, a steroid, a hormone, a coagulant, a sclerosing agent and a cross-linking agent.

10. The method of claim 1, wherein the catheter device defines a lumen and an infusion port, the lumen in communication with the infusion port and configured to deliver the dose of the agent to the segment.

11. The method of claim 10, wherein the infusion port is disposed on the catheter device between the first occluder and the second occluder such that the infusion port can deliver the dose of the agent to the segment isolated between the first occluder and the second occluder.

12. The method of claim 1, wherein treating the target area to reduce the microvasculature in the target area comprises administering a dose of radiation.

13. The method of claim 12, wherein treating the target area comprises administering the dose of radiation wherein the dose of radiation includes an amount of radiation totaling between 20 and 50 gray (Gy).

14. The method of claim 13, wherein the amount of radiation is selected based on one or more characteristics of the tumor, the one or more characteristics of the tumor including at least one of: a location of the tumor, and a size of the tumor.

15. The method of claim 1, wherein administering the dose of the agent occurs after a predefined period of time following treating the target area.

16. The method of claim 15, wherein the predefined period of time is between two weeks and six months.

17. The method of claim 1, wherein the agent includes a dye.

18. A method, comprising:
isolating a segment of a lumen proximate to a target area, wherein the target area includes a tumor that has been devascularized to reduce the microvasculature in the target area;
decreasing an intraluminal pressure of the segment to a level of pressure of an interstitial space between the lumen and the target area; and
delivering a dose of an agent to the devascularized target area from the isolated segment while increasing the intraluminal pressure to greater than the pressure of the interstitial space between the lumen and the target area.

19. The method of claim 18, wherein the segment of the lumen is isolated using a catheter device including a first occluder and a second occluder, wherein distance between the first occluder and the second occluder is adjustable.

20. The method of claim 19, wherein the catheter device further includes a pressure sensor configured to measure the intraluminal pressure of the segment.

21. A method, comprising:
inserting a catheter device into a lumen within or adjacent to a tumor wherein the tumor is in a target area that has been treated to reduce a microvasculature in the target area, the catheter device including a first occluder and a second occluder;
isolating a segment of the lumen proximate to the target area using the first occluder and the second occluder;
delivering a dose of an agent to the target area having the reduced microvasculature from the isolated segment via the catheter device.

* * * * *